(12) United States Patent
Cohn

(10) Patent No.: US 12,006,395 B2
(45) Date of Patent: Jun. 11, 2024

(54) BIODEGRADABLE POLYMER

(71) Applicant: YISSUM RESEARCH DEVELOPMENT COMPANY OF THE HEBREW UNIVERSITY OF JERUSALEM LTD, Jerusalem (IL)

(72) Inventor: Daniel Cohn, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 15/540,201

(22) PCT Filed: Dec. 31, 2015

(86) PCT No.: PCT/IL2015/051272
§ 371 (c)(1),
(2) Date: Jun. 27, 2017

(87) PCT Pub. No.: WO2016/108242
PCT Pub. Date: Jul. 7, 2016

(65) Prior Publication Data
US 2017/0369628 A1 Dec. 28, 2017

Related U.S. Application Data

(60) Provisional application No. 62/099,238, filed on Jan. 2, 2015.

(51) Int. Cl.
| | |
|---|---|
| C08G 18/42 | (2006.01) |
| A61K 47/34 | (2017.01) |
| A61L 15/26 | (2006.01) |
| A61L 17/10 | (2006.01) |
| A61L 17/12 | (2006.01) |
| A61L 27/18 | (2006.01) |
| A61L 27/34 | (2006.01) |
| A61L 31/06 | (2006.01) |
| A61L 31/10 | (2006.01) |
| C08G 18/48 | (2006.01) |
| C08G 18/73 | (2006.01) |
| C08G 18/74 | (2006.01) |
| C08G 18/76 | (2006.01) |
| C08G 63/664 | (2006.01) |
| C08G 63/685 | (2006.01) |
| C08G 63/91 | (2006.01) |
| C08L 67/04 | (2006.01) |

(52) U.S. Cl.
CPC ............. *C08G 18/42* (2013.01); *A61L 15/26* (2013.01); *A61L 17/10* (2013.01); *A61L 17/12* (2013.01); *A61L 27/18* (2013.01); *A61L 27/34* (2013.01); *A61L 31/06* (2013.01); *A61L 31/10* (2013.01); *C08G 18/4277* (2013.01); *C08G 18/4825* (2013.01); *C08G 18/73* (2013.01); *C08G 18/74* (2013.01); *C08G 18/76* (2013.01); *C08G 63/664* (2013.01); *C08G 63/685* (2013.01); *C08G 63/6852* (2013.01); *C08G 63/91* (2013.01); *C08G 63/912* (2013.01); *A61K 47/34* (2013.01); *C08G 2220/00* (2013.01); *C08G 2230/00* (2013.01)

(58) Field of Classification Search
CPC ........... A61L 67/04; C08L 71/02; C08L 31/10
See application file for complete search history.

(56) References Cited

U.S. PATENT DOCUMENTS

| | | | | |
|---|---|---|---|---|
| 5,352,515 | A * | 10/1994 | Jarrett | C08G 63/664 428/357 |
| 8,030,413 | B2 * | 10/2011 | Lee | C08G 65/33389 525/328.2 |
| 2004/0156819 | A1 * | 8/2004 | Cohn | A61K 31/765 424/78.38 |
| 2004/0225077 | A1 * | 11/2004 | Gravett | A61L 31/145 525/418 |
| 2007/0003592 | A1 | 1/2007 | Hissink | |
| 2007/0275034 | A1 | 11/2007 | Shalaby et al. | |
| 2008/0247987 | A1 * | 10/2008 | Liggins | A61K 9/0014 424/78.17 |
| 2012/0107366 | A1 * | 5/2012 | Kapiamba | A61P 1/00 424/400 |

FOREIGN PATENT DOCUMENTS

| | | |
|---|---|---|
| EP | 2275150 A2 | 1/2011 |
| EP | 1 752 481 A1 | 9/2017 |
| WO | 99/02168 A1 | 1/1999 |
| WO | 10/026590 A2 | 3/2010 |

OTHER PUBLICATIONS

Zgola et al., Chemosphere, 64, 2006, 803-809.*
R.W. Paynter et al., The Hydrolytic Stability of Mitrathane (a Polyurethane Urea)—an X-Ray Photoelectron Spectroscopy Study, Journal of Biomedics Materials Research, vol. 22, 1988, pp. 687-698.
Kimberly A. Chaffin et al., Polyether Urethane Hydrolytic Stability After Exposure to Deoxygenated Water, Macromolecules, 47, 2014, pp. 5220-5226.
C.S. Schollenberger et al., Thermoplastic Polyurethane Hydrolysis Stability, Die Angewandte Makromolekulare Chemie, 29/30, 1973, pp. 413-430.

(Continued)

*Primary Examiner* — Kyle A Purdy

(74) *Attorney, Agent, or Firm* — BROWDY AND NEIMARK, PLLC

(57) ABSTRACT

The invention provides a class of polymeric materials being ABA tri-block or AB di-block, comprised of biodegradable segments and poly(propylene oxide) (PPO) segment and uses thereof.

15 Claims, 4 Drawing Sheets

(56) References Cited

OTHER PUBLICATIONS

John W. Boretos et al., Segmented Polyurethane: A Polyether Polymer. An Initial Evaluation for Biomedical Applications, J. Biomed. Mater. Res., col. 2, 1968, pp. 121-130.

* cited by examiner

| Product name | Color | Tensile strength |
|---|---|---|
| Maxon | Green/clear | 42 days |
| V-Loc 180 | Violet/clear | 21 days |
| PDS II | Violet/clear | 42 days |
| Biosyn | Violet/clear | 21 days |
| V-Loc 90 | Violet/clear | 14 days |
| Monocryl | Clear | 14 days |
| Caprosyn | Beige | 10 days |
| Vicryl Rapide | Violet/beige | 5 days |
| Polysorb | Violet/beige | 21 days |
| Vicryl | Bi-color Green and White/beige | 28 days |
| Dexon | | 21 days |

Less than 7 weeks!

FIG. 1A

BIODEGRADABLE POLYMER

TECHNOLOGICAL FIELD

The invention generally concerns a novel class of polymers and uses thereof, e.g., in the construction of medical devices such as sutures.

BACKGROUND OF THE INVENTION

As many as 20% of patients that undergo abdominal wall opening (Laparotomy) surgery will develop a pathology called Post Operative Ventral Hernia (POVH) within 5 years. POVH means that the intestines normally contained within the abdominal wall burst through this tissue, resulting in agonizing pain, disfiguration and even death, as the intestines may get strangulated.

The normal healing of the abdominal wall is such that within two months of closure, it regains 80% of its original strength. Gold standard surgical sutures provide up to two months of tissue support. Three main factors contribute to the appearance of POVH: (1) errors by the physician, (2) physiology of the patient, and (3) inappropriate use of closure material. The most important factor for POVH seems to be the physiology of the patient. Studies show that the chances of effective wound healing are greatly reduced in patients that are immune-suppressed, the elderly, patients undergoing chemotherapy, patients under steroid therapy and a great variety of other patients.

The way to overcome this risk factor and reduce the occurrence of POVH is by increasing the support to the tissue, allowing it more time to heal. One such support is commonly provided by sutures, traditionally used in surgery e.g., to close a wound, for holding tissues together in a variety of surgical procedures. Every absorbable suture has an absorption profile that stipulates the time it takes the suture to fully degrade and evacuate from the body. The medical consensus is for the suture to remain in the tissue for as a minimal a period as possible after fulfilling its intended purpose. The intended purpose of an absorbable suture is measured by the suture's ability to maintain sufficient tensile-strength until the intended tissue is self-sufficient.

As mentioned, 80% of patients admitted for surgery are immune-compromised which means that normal sutures that provide 2 months of support will not provide tensile strength long enough to allow the abdominal wall to heal and reach a self-supporting stage. Research suggests that immuno-compromised patients require prolonged support to the abdominal wall, in the range of 3-5 months, to allow sufficient healing of the abdominal wall. Such a suture that also features a fast absorption rate will help minimize POVH related to insufficient tissue support in immune-compromised patient.

SUMMARY OF THE INVENTION

Thus, for the purpose of providing a superior class of sutures, and other medical devices, that would lack the deficiencies associated with currently available equivalents, the inventor of the technology disclosed herein has developed a novel and unique class of biodegradable polymers that can be manipulated in composition, structure and form to suit a great variety of medical and other purposes.

As known in the art, the rate of polymer degradation, which depends on a variety of parameters, will increase as a function on the polymer's hydrophilicity. In other words, one expects to observe increased degradation in polymers of higher hydrophilicities. This is typically due to the fact that more hydrophilic polymers attract more (or more rapidly) water molecules that hydrolyze the groups responsible for the degradation; such groups may be aliphatic ester groups, which are present along the polymeric backbone, resulting in chain cleavage and, concomitantly, in the decrease of the polymer molecular weight.

An additional key factor is the degree of crystallinity of the polymer. Since crystalline phases, which consist tight arrays of the polymeric chains, are more compact and dense, when compared to the amorphous more open equivalents, the diffusion of water molecules into the crystalline phase is significantly hindered. As a result, the higher the crystallinity of the degradable polymer is, the slower its degradation.

All other parameters being equal, a polymer comprising a hydrophilic polyethylene oxide (PEO) segment is expected to degrade faster than its counterpart comprising a hydrophobic polypropylene oxide (PPO) segment.

The inventor of the present invention has developed a unique class of tri-block and di-block hydrophobic polymers, which against the above well known fact, degrade and behave as their hydrophilic counterparts. This "switched" or "reversed" behavior, not expected in the novel class of polymers of the invention, is believed to stem from the unique arrangement of the polymer segments, as further disclosed herein.

The polymers of the invention have a tri-block or di-block structure of various molecular weights, having a central PPO segment and two (tri-block) or one (di-block) lateral bioabsorbable segments, e.g., polycaprolactone (PCL) segments, that are chain extended (tri-block) or coupled (di-block) using a variety of bifunctional reactive molecules. When the polymers of the invention contain PCL segments, these polymers are denoted PPCA. Surprisingly, PPCA polymers were found to degrade at the same rate as their polyethylene oxide containing counterparts (PECA). This holds for a range of ethylene oxide/caprolactone (EO/CL) and propylene oxide/caprolactone (PO/CL) ratios.

The polymers of the present invention, as exemplified for PPCA polymers, are described as per the following nomenclature: The name of the polymer, PPCA, will be followed by the molecular weight of the PPO segment, separated from the ratio between the number of the PPO repeating units present in the PPO segment, divided by the number of CL units, present in the tri-blocks (both lateral segments) or di-blocks.

Thus, for example, PPCA 2,000/0.1 designates a PPCA polymer (constructed of a central PPO segment and two PCL segments that are optionally chain extended, cross-linked or coupled, using a variety of functional reactive molecules) having a molecular weight of 2,000 Da and characterized by a ratio of 0.1 between the number of the PPO repeating units (present in the PPO segment) divided by the number of CL units.

Both PECA 2,000/0.1, being a comparative polymer used in the analysis of PPCA 2000/0.1 and the latter, a polymer according to the invention, degrade at a similar rate, even though PECA 2,000/0.1 absorbs three times as much water than PPCA 2,000/0.1. This observation is remarkable, not only in view of the fact that a more hydrophobic polymer exhibits essentially the same degradation rate that of a less hydrophobic polymer or a more hydrophilic polymer, but also when considering the fact that the PECA polymer is more crystalline than its PPCA counterpart. This is demonstrated by the fact that the PECA polymer has a degree of crystallinity of 26% and displays a melting point at 54° C., whereas its PPCA counterpart, a polymer according to the invention, has a degree of crystallinity of 38% and displays a melting point at 58° C. This surprising observation means that the PCL segments present in PPCA are 46% more crystalline than the PCL segments, having the same length, present in PECA.

The presence of the PEO segment, which has a degree of crystallinity of its own, curtails the ability of the PCL to crystallize, whereas the amorphous, highly flexible PPO segment, allows PCL to crystallize better. In the case of PECA, the central segment hinders PCL's ability to crystallize, whereas in the case of PPCA, the central segment enhances mobility and crystallinity.

Also, at time zero, meaning when dry, the polymers of the invention have been found to be 13% stronger than their PECA counterparts. PECA polymers displayed an increase in stiffness (their Young's modulus increased by more than 50%, after 120 days), which when used as sutures for medical purposes, can result in the unravelling of the suturing knot. The polymers of the invention have been found to be suitably flexible during suturing and better suited for wound closure and other clinical indications.

Thus, in a first aspect, there is provided a polymeric material selected from ABA tri-block and AB di-block polymers, wherein A is a biodegradable segment and B is a poly(propylene oxide) (PPO) segment.

Also contemplated are biodegradable polymeric materials comprising PPO segments and biodegradable components. Further provided are biodegradable polymeric materials comprising PPO segments and biodegradable aliphatic polyester components.

Further contemplated are biodegradable polymeric materials, comprising PPO segments(s) and one or more aliphatic polyester component(s), each of which being chain extended and/or coupled and/or cross-linked.

In some embodiments, the polymeric materials of the invention may be generally described as being selected from ABA tri-blocks and AB di-blocks, wherein A is a biodegradable segment and B is a poly(propylene oxide) (PPO) segment, wherein the polymeric material is optionally chain extended, coupled or cross-linked using a chain extender (or bond), a coupling segment (or bond) or cross-linking segment (or bond), respectively.

The term "polymer" is used to describe a material as known in the art, having an average molecular weight from about 1,000-3,000 to several millions, e.g., 5 million or more Daltons (Da), including oligomers of relatively low molecular weights.

In some embodiments, the molecular weight is between 1,000 and 100,000 Da, between 1,000 and 90,000 Da, between 1,000 and 80,000 Da, between 1,000 and 70,000 Da, between 1,000 and 60,000 Da, between 1,000 and 50,000 Da, between 1,000 and 40,000 Da, between 1,000 and 30,000 Da, between 1,000 and 20,000 Da, between 1,000 and 10,000 Da, between 1,000 and 9,000 Da, between 1,000 and 8,000 Da, between 1,000 and 7,000 Da, between 1,000 and 6,000 Da, between 1,000 and 5,000 Da, between 1,000 and 4,000 Da, between 1,000 and 200,000 Da, between 1,000 and 300,000 Da, between 1,000 and 400,000 Da, between 1,000 and 500,000 Da, between 1,000 and 600,000 Da, between 1,000 and 700,000 Da, between 1,000 and 800,000 Da, between 1,000 and 900,000 Da, between 1,000 and 1,000,000 Da, between 1,000 and 2,000,000 Da, between 1,000 and 3,000,000 Da, between 1,000 and 4,000,000 Da, between 1,000 and 1,500,000 Da, between 1,000 and 2,500,000 Da, between 1,000 and 3,500,000 Da, or between 1,000 and 4,500,000 Da.

The polymers of the invention are "tri-blocks" or "di-blocks".

The tri-block polymers of the invention have the general structure ABA, comprising a first polymer, being A block, which in some embodiments is a polyester segment, covalently linked to a poly(propylene), being B block, which is covalently linked to a second polymer segment, being a second A block, which may independently be a polyester segment as well, as depicted in the general tri-block of the formula ABA. The two A blocks need not be the same.

Tri-blocks according to the present invention may be terminated by one or more hydroxyl, amine, or carboxyl moieties or combinations thereof, to enable their further extension or association with other materials. In some embodiments, the polymers are terminated with hydroxyl groups which can be readily covalently linked to chain extenders, cross-linking agents or other groups, optionally containing electrophilic moieties, thereby enabling facile production of a variety of polymers according to the invention.

The term di-block polymers, being of the general structure AB, comprise a first polymer, the A block, being in some embodiments, a polyester segment such as poly(hydroxy carboxylic acid) polyester, covalently linked to a poly(propylene), being B block, as described above.

The terms "segment" and "block" will be used throughout this document, interchangeably. Each segment or block may be the same or different. For instance, each of the biodegradable segments, A, may be the same or different.

The "poly(hydroxy carboxylic acid)" is a unit derived from an aliphatic hydroxy carboxylic acid or a related ester or dimeric ester, including a cyclic dimeric ester, such as, for example, lactic acid, lactide, glycolic acid, glycolide, or a related aliphatic hydroxycarboxylic acid or lactones, such as, for example, ε-caprolactone, δ-glutarolactone, δ-valerolactone, γ-butyrolactone and mixtures, thereof, among numerous others as set forth herein.

The term "biodegradable" generally refers to the ability of polymers of the invention to degrade in the body. When stated in reference to segments A, the term refers to the ability of the molecular segments defining the A blocks to biodegrade in the body and cause degradation of the polymer as a whole.

The polymers according to the present invention degrade in vivo and breakdown into monomeric units such as hydroxy acids. The degradation of the present polymers mainly takes place through the hydrolysis of reactive bonds in the A block, such as aliphatic esters. The hydrolysis reaction is generally dependent upon pH. The rate constant for hydrolysis tends to be much higher at higher pH (greater than 9.0) and lower pH (less than 3.0), than at neutral pH (6.0 to 8.0).

In the case of hydrophilic, in some instances, water-soluble chain extenders and cross-linking agents which may be utilized in gels and viscous solutions according to the present invention, these chain extenders and cross-linking agents, which generally are highly hydrophilic and in some instances highly water-soluble, tend not to be biodegradable. In addition, when using polymers containing A blocks derived from hydroxy acids, the polymeric A blocks will degrade to individual hydroxy acids which are biosynthetically useful and may be involved in the patient's "biochemistry".

In the present invention, the di-blocks may be formed, for example, by initiating a polymerization of hydroxy carboxylic acid (or equivalent monomeric, dimeric or related building blocks) with a hydroxyl, amine or carboxyl-terminated poly(propylene) block which is end-capped (on one end of the polymer) with a non-reactive group. The non-reactive groups may be selected, for example, from alkyl, aryl or aralkyl group or substituted alkyl, aryl or aralkyl group, such as, a $C_1$-$C_{12}$ alkyl group or an equivalent, or a protecting group which can be removed to provide a free nucleophilic moiety at a later stage. The di-blocks which are produced may then be further reacted with chain-extenders, cross-linking agents and the like to produce polymers according to the present invention, having desired or favorable PO/CL ratios. Di-blocks may be used in much the same way that ABA tri-blocks are used in the present invention, i.e., as building polymeric units of the polymers according to the present invention.

The material names "poly(propylene glycol)", "poly(oxypropylene)" and "poly(propylene oxide)", all abbreviated PPO, are used herein interchangeably in describing materials of the invention or used in accordance with the invention. These polymers, of varying molecular weights, are used in the B block of ABA tri-blocks and AB di-blocks as well as chain extenders and cross-linking agents according to the present invention.

The expressions "poly(oxyalkylene) containing" and "poly(propylene oxide) containing" are used to describe certain polymeric chains or segments which contain at least an amount or a number (1 or more) of poly(oxyalkylene) or poly(propylene oxide) units.

The expressions "poly(oxyalkylene) rich" and "poly(propylene oxide) rich" are used to describe certain polymeric materials containing at least 40% by weight of poly(oxyalkylene) or poly(propylene oxide), of the total weight of the polymeric material.

The polymers of the invention, being ABA tri-blocks or AB di-blocks, where A is a biodegradable component, in some instances a polyester, being in some embodiments an oligomer or a polymer comprising degradable units, which are optionally derived from hydroxyacid units or their lactones and the like, and B being based on PPO.

As known in the art, a "polyester" is a unit derived from an aliphatic hydroxy carboxylic acid or a related ester, lactone, dimeric ester, carbonate, anhydride, dioxanone or related monomer, such units may be derived from the following: lactic acid, lactide, glycolic acid, glycolide, or a related aliphatic hydroxycarboxylic acid, ester (lactone), dimeric acid, carbonate, anhydride, orthoester and dioxanone; or related compound such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures thereof.

In some embodiments, used in accordance with the invention are hydroxyacids (such as α-hydroxyacids) and their corresponding cyclic dimeric esters, such as caprolactone, lactide and glycolide.

In some embodiments, the A block material comprises hydroxyacid units derived from an aliphatic hydroxy carboxylic acid or a related acid, ester or similar compound.

In some embodiments, the A block material is selected from lactic acid, lactide, glycolic acid, glycolide, and related aliphatic hydroxycarboxylic acid or ester (lactone) and combinations thereof.

In some embodiments, the A block material is selected from β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures thereof.

In some embodiments, the A block material comprises a poly(hydroxy-carboxylic acid), for example, poly(glycolic acid), poly(L-lactic acid) and poly(D,L-lactic acid) and polycaprolactone, and combinations thereof.

The B block in the tri-blocks and di-blocks of the invention is, in some embodiments, selected from hydroxyl, carboxylic acid or amine terminated poly(propylene oxide) block (being in some embodiments hydroxyl terminated), covering a wide range of molecular weights. In some embodiments, the poly(propylene oxide) block is not linear and may be branched; or have any other spatial configuration that has a functionality (namely the number of reactive end groups) of more than two.

In some embodiments, not all poly(propylene oxide) end groups react with the biodegradable chains, A, typically aliphatic polyester segments, but remain unreacted or react to other components.

The tri-blocks or di-blocks are optionally end-capped with hydroxyl groups and are chain-extended using difunctional chain extenders, such as diisocyanates, dicarboxylates, diesters or diacyl halide groups in order to chain extend the tri-blocks to yield higher molecular weight polymer chains. Alternatively, the tri-blocks may be end-capped with groups such as carboxylic acid or ester moieties (which may be reacted directly as ester groups, activated as "active" ester groups or converted to active acyl groups such as acyl halides) or isocyanate groups or other groups able to react with the terminal groups of difunctional chain extenders or couplers such as diols, diamines, or hydroxylamines, or polyoxyethylene (polyethylene glycol) or poly(ethylene oxide)-co-poly(propylene oxide) block copolymer chain extenders (especially, in the case of water soluble or water dispersible gels, dispersions or viscous solutions) among numerous others, to produce chain extended or coupled polymers having higher molecular weights.

The polymers according to the present invention optionally comprise chain-extended tri-blocks or coupled di-blocks, which have relatively high molecular weights, which cover a range of molecular weights, provide polymeric characteristics which are advantageously employed in fibers, according to the present invention. In some embodiments, said tri-blocks and di-blocks react with molecules of functionalities higher than two.

In certain aspects of the present invention, polymers for use in the present invention have the following characteristics: they are pre-polymerized, chain-extended or coupled, substantially non-cross-linked and biodegradable. In other instances, the polymers may be cross-linked. The polymers of the invention are advantageously used as fibers, sutures and staples. Polymers used in fibrous structures such as sutures according to the present invention are sufficiently strong and flexible to enable the suture to perform satisfactorily over the period of time required, displaying also enhanced suturability and knotability.

In certain aspects of the present invention, the polymers disclosed herein combine tri-blocks and di-blocks. In certain aspects of the present invention, the polymers disclosed herein are chain extended and/or coupled and/or cross-linked, with each of the three alternative pathways being performed simultaneously or sequentially.

In some embodiments, the tri-blocks or di-blocks are first chain extended or coupled and then cross-linked.

In other embodiments, the tri-blocks or di-blocks are first chain extended or coupled, then stretched and the molecules are longitudinally oriented, and then cross-linked.

As used hereinbelow, the polymers of the invention are members of the PPCA family, each member comprising poly(propylene oxide) and poly(caprolactone) blocks, being optionally chain extended, e.g., with a diisocyanate, such as hexamethylene diisocyanate. The PPCA polymers of the invention are generally designated with respect to their composition by the average molecular weight of the poly(propylene oxide) chain and by their PO/CL ratio, where PO is the number of propylene oxide units present and CL is the total number of caprolactoyl units (ester units) present. A general definition of PO/CL ratio is presented hereinbelow.

In some embodiments of the present invention, the ABA tri-block is a substantially water insoluble unit comprising biodegradable blocks, such as poly(hydroxy acid) blocks, and poly(propylene oxide blocks). The A block of the ABA tri-blocks of the present polymers is biodegradable and ranges in size from one monomeric unit (a monomeric unit within the A block being considered caprolactone, lactic acid, glycolic acid or a related hydroxy acid (ester) unit even where caprolactone and/or lactide and/or glycolide or related reactants containing more than one hydroxyacid unit are used to produce the A block) up to several thousand units, for example about 600 or more monomeric units, with the size ranging from about 4 to about 400 units, or from about 10 to about 200 units, which length depends upon the length or molecular weight of the poly(propylene oxide) segment combined with the A block in the tri-blocks. It is to be noted that the size of the A block may well fall outside of the above range, depending upon the overall physical characteristics of the ABA tri-block formed and the size of the B block.

The A block is derived, in some embodiments, from an hydroxyacid as described above, or from units of glycolic acid, lactic acid (L or D, L mixtures to promote biodegradability), caprolactone or mixtures thereof, in the form of glycolide, lactide or caprolactone reactants (as further explained hereinbelow). In certain embodiments, in polymers to be used to manufacture fibers and sutures, the A blocks tend to create hard domains in the matrix and generally provide strength and structural integrity to the polymer. The A block is water-insoluble and is optionally sized in combination with the poly(propylene oxide) segment in order to promote phase separation between the A and B blocks in the ABA tri-block or AB di-block and the final polymer to be used as sutures and in other clinical applications. Thus, the A block instills the final polymer with essential structural characteristics, which, in combination with the B block, results in a polymer having excellent mechanical characteristics and controllable biodegradability. In addition, in certain embodiments according to the present invention, the length of the A block is believed to be important for providing a material with a phase separated microstructure.

The poly(propylene oxide) B block may vary in size from about 100 Da (dalton units) up to about 200,000 Da or higher, or with a range of about 400 Da up to about 20,000 Da. In some embodiments, the poly(propylene oxide) block ranges in size from about 400 to about 10,000 Da. Based upon the teachings of the present invention, one of ordinary skill will know to vary the length of the B block and the A block to provide polymers having excellent properties, which makes them especially suited to perform as wound closure devices, such as sutures and staples, depending upon the type of final formulation desired and the manufacturing process they undergo.

The ABA tri-blocks or AB di-blocks according to the present invention are generally described according to their PO/CL ratio. This ratio is the number of monomeric repeating units of the poly(propylene oxide) B block (the repeating unit being propylene oxide units) divided by the total number of monomeric units in the A block(s). Polymers comprised of ABA tri-blocks or AB di-blocks, which are chain extended, coupled or cross-linked pursuant to the present invention, may also be described in terms of PO/CL ratio for the polymer, in which case the PO/CL ratio simply represents the ratio of propylene oxide units to hydroxy acid monomeric units in the entire polymer.

The PO/CL ratio of the entire polymer may be determined by NMR analysis. These polymers may also be designated with respect to their composition by the average molecular weight of the poly(propylene oxide) (PPO) chain or chains and by the weight percentage of the PPO chain or chains in the tri-block, di-block or total polymer. It should be noted, however, that in instances where the chain extender, coupler or cross-linking agent comprises a poly(propylene oxide) chain, the PO/CL ratio for the polymer may vary considerably from the PO/CL ratio found in the ABA tri-block or AB di-block (the total amount of PO may become considerably larger because of contribution of PO from the chain extender, and consequently, the PO/CL ratio for the polymer may be considerably larger than it is for the ABA tri-block or AB di-block). Likewise, the weight percentage of PPO found in such a polymer may also be quite different from that found in the ABA tri-block or AB di-block.

Without being limited by way of presentation, the concept of the PO/CL ratio may be exemplified by a polymer described as poly(propylene oxide)/polycaprolactone block copolymer (PPCA) 2,000/0.5, which is a hexamethylene diisocyanate chain extended ABA tri-block comprising PPO chains having an average molecular weight of 2,000 Da and a PO/CL ratio of 0.5. The tri-block in this polymer comprises, therefore, a 2,000 molecular weight PPO segment for the B block containing approximately 35 propylene oxide units and two A blocks each containing, on average, approximately 35 CL units. Alternatively, the same polymer can be designated as 2,000/80%, where 2,000 is the average molecular weight of the PPO chains, and 80% is the weight percentage of PCL in the ABA tri-block. For this PPCA 2,000/0.5 polymer, the molecular weight of the tri-block is approximately 7,980 (2,000 for the PPO chain and two polycaprolactone A blocks, each having a molecular weight of approximately 3,990, for a total for the two A blocks of 7,980). The weight percentage of the PPO block in this tri-block is, accordingly, 20% (2,000/9,980).

Alternatively, by way of example, the ABA tri-block described above may be chain extended with a great variety of chain extenders, differing in their composition, molecular weight, degree of hydrophilicity, rigidity, being biodegrdable or not, or displaying other advantageous features, such as rendering the polymer of the invention with stimulus responsiveness. This is exemplified by HDI-PEG4000-HDI, which is formed by reacting a poly(ethylene oxide) chain of molecular weight 4,000, with two moles of hexamethylene diisocyanate. The repeating unit along the backbone, after the reaction of this chain extender with the ABA tri-block described above is:

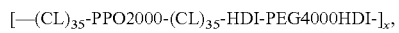

[—(CL)$_{35}$-PPO2000-(CL)$_{35}$-HDI-PEG4000HDI-]$_x$, wherein x denotes the degree of polymerization of the repeating unit; more specifically, the number of repeating units present, on average, per molecule of polymer.

The above can be further exemplified by using an environmentally responsive polymer, end-capped with groups able to react with the end groups of the ABA tri-block. Aiming at rendering the polymer of the invention with reverse thermo-responsiveness, a reverse thermo-responsive polymer, such as a PEO-PPO-PEO triblock, can be end capped with groups able to react with the end groups of the ABA tri-block or the AB di-block, rendering the polymer with the desired additional capability.

The PO/CL ratio for polymers according to the present invention ranges from about 0.05 to about 100 or more, or about 0.1 to about 30, or from about 0.2 to about 10. In certain instances, the PO/CL ratio may fall outside of these ranges, depending upon the final characteristics of the polymers which are desired. The PO/CL ratios for individual polymers may also vary according to the size of the B block and the type of chain-extender which is used. In certain embodiments, as the size (molecular weight) of the B block in the tri-blocks increases, the PO/CL ratio will tend to be somewhat less than in tri-blocks and polymers where the size of the B block is less.

Based upon the teachings of the present invention, one of ordinary skill in the art will know to vary the length of the A block to the B block in a manner which provides polymers having controllable mechanical properties and biodegradability, as defined by its biomedical use.

Thus, with the above in mind, the following embodiments provide polymers for use in accordance with the present invention, in medical and non-medical applications.

In some embodiments, in a tri-block or di-block of the invention A is a polymer comprising aliphatic ester units. In some embodiments, the aliphatic ester units are derived from hydroxyl acid units, or from their related esters or lactones.

In some embodiments, A is a polymer segment comprising at least one of lactic acid; lactide; glycolic acid; glycolide; an aliphatic hydroxycarboxylic acid or ester (lactone) selected from β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione; cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid; salicylic acid and mixtures thereof.

In some embodiments, A comprises poly(glycolic acid), poly(L-lactic acid), poly(D,L-lactic acid) or polycaprolactone or any combination thereof.

In some embodiments, the B block comprises hydroxyl, carboxylic acid or amine terminated PPO segment(s).

In some embodiments, B comprises poly(propylene oxide) and each of A comprises poly(caprolactone).

In some embodiments, the ABA tri-block or AB di-block polymers are chain extended or coupled using at least one difunctional compound, which is capable of reacting with an end-cap group of the tri-block or di-block. In some embodiments, said difunctional compounds are diisocyanates. In some embodiments, said diisocyanates is hexamethylene diisocyanate (HDI).

In some embodiments, said difunctional compounds comprise two molecular segments having functionality and a middle segment connecting said two molecular segments. In some embodiments, said middle segment is a polyoxyalkylene. In some embodiments, said middle segment is a polyester.

In some embodiments, said polyoxyalkylene is polyethylene oxide, polypropylene oxide, polytetramethylene oxide or any combination or a copolymer thereof.

In some embodiments, said polyester is a polycaprolactone, a polylactic acid, a polyglycolic acid, or any combination or a copolymer thereof.

In some embodiments, said difunctional compounds are selected from diisocyanates. In some embodiments, said diisocyanate is hexamethylene diisocyanate (HDI).

In some embodiments, the polymer of the invention is selected amongst polymers of Formula (I):

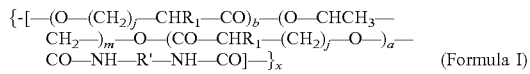

{-[—(O—(CH$_2$)$_j$—CHR$_1$—CO)$_b$—(O—CHCH$_3$—CH$_2$—)$_m$—O—(CO—CHR$_1$—(CH$_2$)$_j$—O—)$_a$—CO—NH—R'—NH—CO]—}$_x$   (Formula I)

wherein
each a and b, independently of the other, is an integer between 1 and 2,000,
m is an integer between 2 and 1,000,
each j, independently of the other, is an integer between 0 and 20,
R' is selected from C$_2$-C$_{20}$ alkylene, C$_5$-C$_{20}$ cycloalkyl, C$_5$-C$_{20}$ cycloalkyl-containing group, aryl, aryl-containing group, polymeric segment, oligomeric segment,
each R$_1$, independently of the other, is H or C$_1$-C$_{12}$ alkyl, and wherein
x is an integer defining the number of repeating units in a polymer of the invention, x may be between 1 and 1,000.

In some embodiments, x is between 1 and 900, between 1 and 800, between 1 and 700, between 1 and 600, between 1 and 500, between 1 and 400, between 1 and 300, between 1 and 200, between 1 and 100, between 10 and 900, between 20 and 900, between 30 and 900, between 40 and 900, between 50 and 900, between 60 and 900, between 70 and 900, between 80 and 900, between 90 and 900, between 100 and 900, between 200 and 900, between 300 and 900, between 400 and 900, or between 500 and 900.

In some embodiments, a is between 1 and 1,400, between 1 and 1,000, between 1 and 500, between 1 and 200, between 1 and 100, between 1 and 90, between 1 and 80, between 1 and 70, between 1 and 60, between 1 and 50, between 1 and 40, between 1 and 30, between 1 and 20, or between 1 and 10.

In some embodiments, b is between 1 and 1,400, between 1 and 1,000, between 1 and 500, between 1 and 200, between 1 and 100, between 1 and 90, between 1 and 80, between 1 and 70, between 1 and 60, between 1 and 50, between 1 and 40, between 1 and 30, between 1 and 20, or between 1 and 10.

In some embodiments, m is between 2 and 900, between 2 and 500, between 2 and 200, between 2 and 100, between 2 and 90, between 2 and 80, between 2 and 70, between 2 and 60, between 2 and 50, between 2 and 40, between 2 and 30, between 2 and 20, or between 2 and 10.

In some embodiments, j is 0. In some embodiments, j is 1, 2, 3, 4, 5, 6, 7, 8, 9, or 10.

In some embodiments, a and b are the same. In some embodiments, a and b are different.

In some embodiments, all integers j are the same.

In some embodiments, R' is an aryl selected from napthyl and phenyl. In other embodiments, R' is selected from 4,4'-diphenylmethane, 3,3'-dimethylphenyl, 3,3'-dimethyldiphenylmethane, 4,6'-xylylene and p-phenylene.

In some embodiments, R' is a $C_2$-$C_{12}$ alkylene or a $C_5$-$C_{12}$ cycloalkyl. In some embodiments, R' is selected from 4,4'-dicyclohexylmethane, isophorone, lysine, cyclohexyl, 3,5,5-trimethylcyclohexyl and 2,2,4-trimethylhexamethylene.

In some embodiments, R' is a polymeric segment or an oligomeric segment. The polymeric segment or an oligomeric segment being optionally selected from polypropylene oxide, polypropylene oxide-containing chain, polypropylene oxide-rich chain, polytetramethylene oxide, polytetramethylene oxide-containing chain, polytetramethylene oxide-rich chain, polyethylene oxide, polyethylene oxide-containing chain, polyethylene oxide-rich, copolymers of polyethylene oxide and polypropylene oxide, polydimethylsiloxane, polydimethylsiloxane-containing chain, polydimethylsiloxane-rich, polycaprolactone, polycaprolactone-containing chain and polycaprolactone rich chain, olipeptide, oligopeptide-containing chain, oligopeptide-rich chain, oligosaccharide, oligosaccharide-containing chain, oligosaccharide rich chain, oligomer or polymers and copolymers of addition polymers, and combinations thereof.

In some embodiments, j=0. In other embodiments, $R_1$ is —$CH_3$. In further embodiments, $R_1$ is —H.

In some embodiments, R' is isophorone or lysine.

In some embodiments, j=0 and $R_1$ is —H.

In some embodiments, j=0 and $R_1$ is —$CH_3$.

In some embodiments, R' is a hexamethylene group ($C_6$ alkylene group), j=4 and $R_1$ is —H.

In some embodiments, the polymer of the invention is selected amongst polymers of Formula (II):

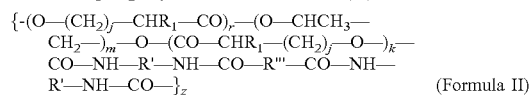

$\{-(O—(CH_2)_j—CHR_1—CO)_r—(O—CHCH_3—CH_2—)_m—O—(CO—CHR_1—(CH_2)_j—O—)_k—CO—NH—R'—NH—CO—R'''—CO—NH—R'—NH—CO—\}_z$ (Formula II)

wherein
each r and k, independently of the other, is an integer between 1 and 2,000,
m is an integer between 2 and 1,000,
each j, independently of the other, is an integer between 0 and 20,
each R', independently of the other, is selected from $C_2$-$C_{20}$ alkylene, $C_5$-$C_{20}$ cycloalkyl, $C_5$-$C_{20}$ cycloalkyl-containing group, aryl, aryl-containing group, polymeric segment, oligomeric segment, and
R''' is selected from polymeric segment and oligomeric segment,
each $R_1$ is H or $C_1$-$C_{12}$ alkyl,
z is an integer defining the number of repeating units in a polymer of the invention, z may be between 1 and 1,000.

In some embodiments, z is between 1 and 900, between 1 and 800, between 1 and 700, between 1 and 600, between 1 and 500, between 1 and 400, between 1 and 300, between 1 and 200, between 1 and 100, between 10 and 900, between 20 and 900, between 30 and 900, between 40 and 900, between 50 and 900, between 60 and 900, between 70 and 900, between 80 and 900, between 90 and 900, between 100 and 900, between 200 and 900, between 300 and 900, between 400 and 900, or between 500 and 900.

In some embodiments, r is between 1 and 1,400, between 1 and 1,000, between 1 and 500, between 1 and 200, between 1 and 100, between 1 and 90, between 1 and 80, between 1 and 70, between 1 and 60, between 1 and 50, between 1 and 40, between 1 and 30, between 1 and 20, or between 1 and 10.

In some embodiments, k is between 1 and 1,400, between 1 and 1,000, between 1 and 500, between 1 and 200, between 1 and 100, between 1 and 90, between 1 and 80, between 1 and 70, between 1 and 60, between 1 and 50, between 1 and 40, between 1 and 30, between 1 and 20, or between 1 and 10.

In some embodiments, m is between 2 and 900, between 2 and 500, between 2 and 200, between 2 and 100, between 2 and 90, between 2 and 80, between 2 and 70, between 2 and 60, between 2 and 50, between 2 and 40, between 2 and 30, between 2 and 20, or between 2 and 10.

In some embodiments, j is 0.

In some embodiments, j is 1, 2, 3, 4, 5, 6, 7, 8, 9, or 10.

In some embodiments, R' is an aryl selected from napthyl and phenyl. In other embodiments, R' is selected from 4,4'-diphenylmethane, 3,3'-dimethylphenyl, 3,3'-dimethyldiphenylmethane, 4,6'-xylylene and p-phenylene.

In some embodiments, R' is a $C_2$-$C_{12}$ alkylene or a $C_5$-$C_{12}$ cycloalkyl. In some embodiments, R' is selected from 4,4'-dicyclohexylmethane, cyclohexyl, 3,5,5-trimethylcyclohexyl and 2,2,4-trimethylhexamethylene.

In some embodiments, R' is a polymeric segment or an oligomeric segment selected from polypropylene oxide, polypropylene oxide-containing chain, polypropylene oxide-rich chain, polytetramethylene oxide, polytetramethylene oxide-containing chain, polytetramethylene oxide-rich chain, polyethylene oxide, polyethylene oxide-containing chain, polyethylene oxide-rich, copolymers of polyethylene oxide and polypropylene oxide, polydimethylsiloxane, polydimethylsiloxane-containing chain, polydimethylsiloxane-rich, polycaprolactone, polycaprolactone-containing chain and polycaprolactone rich chain, olipeptide, oligopeptide-containing chain, oligopeptide-rich chain, oligosaccharide, oligosaccharide-containing chain, oligosaccharide rich chain, oligomer or polymers and copolymers of addition polymers, and combinations thereof.

In some embodiments, R''' is a polymeric segment or an oligomeric segment selected from polypropylene oxide, polypropylene oxide-containing chain, polypropylene oxide-rich chain, polytetramethylene oxide, polytetramethylene oxide-containing chain, polytetramethylene oxide-rich chain, polyethylene oxide, polyethylene oxide-containing chain, polyethylene oxide-rich, copolymers of polyethylene oxide and polypropylene oxide, polydimethylsiloxane, polydimethylsiloxane-containing chain, polydimethylsiloxane-rich, polycaprolactone, polycaprolactone-containing chain and polycaprolactone rich chain, olipeptide, oligopeptide-containing chain, oligopeptide-rich chain, oligosaccharide, oligosaccharide-containing chain, oligosaccharide rich chain, oligomer or polymers and copolymers of addition polymers, and combinations thereof.

Further embodiments relating to Formula (II) are identical to those provided herein in reference to Formula (I) or any other Formula.

In some embodiments, the polymer of the invention is selected amongst polymers of Formula (III):

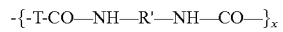

-$\{$-T-CO—NH—R'—NH—CO—$\}_x$ (Formula III)

wherein

T is $\{-(O-(CH_2)_j-CHR_1-CO)_r-(O-CHCH_3-CH_2-)_m-O-(CO-CHR_1-(CH_2)_j-O-)_k\}_p$,

R' is selected from $C_2$-$C_{20}$ alkylene, $C_5$-$C_{20}$ cycloalkyl, $C_5$-$C_{20}$ cycloalkyl-containing group, aryl, aryl-containing group, polymeric segment, oligomeric segment, p is an integer between 1 and 100, each r and k, independently of the other, is an integer between 1 and 500, m is an integer between 2 and 100, each j, independently of the other, is an integer between 0 and 10, $R_1$ is H or $C_1$-$C_{12}$ alkyl, and x is an integer defining the number of repeating units in a polymer of the invention, x may be between 1 and 300.

All embodiments relating and provided herein in reference to Formulae (I) and (II) are equivalently relevant also to Formula (III).

In some embodiments, the polymer of the invention is selected amongst polymers of Formula (IV):

HOOC-T-COOH          (Formula IV)

wherein

T is $\{-(O-(CH_2)_j-CHR_1-CO)_r-(O-CHCH_3-CH_2-)_m-O-(CO-CHR_1-(CH_2)_j-O-)_k\}_p$, p is an integer between 1 and 100, each r and k, independently of the other, is an integer between 1 and 500, m is an integer between 2 and 100, each of j, independently of the other, is an integer between 0 and 10, and R1 is H or $C_1$-$C_{12}$ alkyl.

All embodiments relating and provided herein in reference to Formulae (I) and (II) and (III) are equivalently relevant also to Formula (IV).

In some embodiments, the polymer of the invention is selected amongst polymers of Formula (V):

-{-T-CO—NH—R'—CO—NH—R'—NH—CO—R'''—CO—NH—R'—NH—CO—}$_z$      (Formula V)

wherein

T is $\{-(O-(CH_2)_j-CHR_1-CO)_r-(O-CHCH_3-CH_2-)_m-O-(CO-CHR_1-(CH_2)_j-O-)_k\}_p$, each R', independently of the other, is selected from $C_2$-$C_{12}$ alkylene, $C_5$-$C_{12}$ cycloalkyl, cycloalkyl-containing group, aryl, aryl-containing group, polymeric segment, oligomeric segment, R''' is selected from polymeric segment and oligomeric segment, z is an integer defining the number of repeating units in a polymer of the invention, z may be between 1 and 300, p is an integer between 1 and 100, each r and k, independently of the other, is an integer between 1 and 500, m is an integer between 2 and 100, each of j, independently of the other, is an integer between 0 and 10, and $R_1$ is H or $C_1$-$C_{12}$ alkyl.

All embodiments relating and provided herein in reference to Formulae (I) and (II) and (III) and (IV) are equivalently relevant also to Formula (V).

In some embodiments, each of the polymers of the invention may be chain extended or coupled by an extender of Formula (VI):

L'-OC—R''—CO-L          (Formula VI)

wherein

R'' is selected from $C_0$-$C_{12}$ alkylene, optionally substituted by one or more hydroxyl group and/or carboxylic acid group and/or amine group, $C_2$-$C_{10}$ alkene, $C_5$-$C_{12}$ cycloalkyl, optionally substituted by one or more hydroxyl group and/or carboxylic acid group and/or amine group, aryl, aryl-containing group, and L and L', independently of the other, may be selected from hydroxyl (—OH), a halide (e.g., Cl, I, Br), amine and an ester group.

As used herein, the term "alkyl" refers to any saturated, monovalent unbranched or branched hydrocarbon chain. The alkyl group may be regarded as a "$C_1$-$C_{12}$alkyl", comprising between 1 and 12 carbon atoms, or any longer chain. Non-limiting examples of such alkyl groups include methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, iso-pentyl, neo-pentyl, hexyl, heptyl, and octyl. Any one alkyl group may be substituted or unsubstituted, where substitution is present, it may include one or two suitable substituents selected from a halide, —OH, an amine (primary, secondary or tertiary), carboxylic acid and others.

Where the alkyl chain is a mid-chain segment, it is referred to as an "alkylene" having any number of carbon atoms. The term "$C_2$-$C_{20}$ alkylene" refers to a mid-chain hydrocarbon segment comprising between 2 and 20 carbon atoms.

In some embodiments, the alkyl group, unless otherwise specifically designated, comprises 1, 2, 3, 4, 5, 6, 7, 8, 9, 10, 11, 12, 13, 14, 15, 16, 17, 18, 19 or 20 carbon atoms in a linear chain, branched chain or any other arrangement, wherein the number of hydrogen atoms depend on the specific arrangement of the carbon chain. In some embodiments, the alkyl group comprises between 1 and 12 carbon atoms. In some embodiments, the alkyl group comprises between 1 and 20 carbon atoms, between 1 and 10 carbon atoms, between 1 and 5 carbon atoms, or between 5 and 15 carbon atoms.

A "cycloalkyl" refers to a monocyclic or polycyclic ring comprising carbon and hydrogen atoms and having no unsaturation. A cycloalkyl group may contain between 5 and 20 carbon atoms and may be a monocyclic ring structure such as cyclopentyl, cyclohexyl and cycloheptyl (or their equivalent cycloalkylene moieties) or a polycyclic ring structure, and may be unsubstituted or substituted with one or more suitable substituents. In some embodiments, the cycloalkyl group is a monocyclic or bicyclic ring, comprising from 3 to 6 carbon atoms. A "cycloalkyl-containing group" is any group containing or associated with a cycloalkyl group as herein defined.

As used herein, an "aryl" means a monocyclic or polycyclic-aromatic group comprising carbon atoms and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group may be unsubstituted or substituted with one or more suitable substituents. In some embodiments, the aryl group is a monocyclic ring, comprising 6 or 10 carbon atoms. In some embodiments, the aryl is napthyl or phenyl, or any substituted form thereof. An "aryl-containing group" is any group containing or associated with an aryl group as herein defined.

In some embodiments, the aryl group is a "heteroaryl" group. The heteroaryl groups comprises a monocyclic- or polycyclic aromatic ring, as defined herein, and one to 3 heteroatoms selected from nitrogen, oxygen, and sulfur. Such heteroaryls may be selected for example from pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, furyl, phienyl, isoxazolyl and oxazolyl. In some embodiments, the heteroaryl group is a monocyclic ring comprising between 2 and 5 carbon atoms and 1 to 3 heteroatoms.

As used herein, an "ester group" is generally of the form $R_y$—O—C(O)—$R_x$ or $R_y$—C(O)—O—$R_x$, wherein each of $R_x$ and $R_y$, independently, being a point of connectivity in a compound of the invention, which may be the same or a different carbon chain, optionally being an alkyl or alkylene group, as specified or defined herein. In some embodiments, an ester group is one which is a product of hydroxyl-alkyl, hydroxyl-phenyl, hydroxyl-benzyl or substituted hydroxyl-alkyl, hydroxyl-phenyl or hydroxyl-benzyl, including activated ester groups such as a tosyl group, a mesyl group or a related activated group, with an alkyl-, aryl-acid.

In some embodiments, the polymers of the invention are selected amongst those having a PO/CL ratio ranging from about 0.05 to about 100, from about 0.1 to about 30, or from about 0.2 to about 10.

In some embodiments, the polymers of the invention are selected amongst those having a PO/CL ratio between about 0.1 and about 30, or between 0.1 to 20, or between 0.1 to 10, or between 0.1 to 5, or between 0.1 to 4, or between 0.1 to 3, or between 0.1 to 2, or between 0.1 to 1, or between about 0.2 and about 10.

In some embodiments, the polymer is a tri-block polymer having a PO/CL ratio between 0.05 and 8.

In some embodiments, the PO/CL ratio is between 0.1 and 5, between 0.1 and 4, between 0.1 and 3, between 0.1 and 2, between 0.1 and 1, between 0.1 and 0.9, between 0.1 and 0.8, between 0.1 and 0.7, between 0.1 and 0.6, between 0.1 and 0.5, between 0.1 and 0.4, between 0.1 and 0.3, between 0.1 and 0.2, between 0.2 and 5, between 0.3 and 5, between 0.4 and 5, between 0.5 and 5, between 0.6 and 5, between 0.7 and 5, between 0.8 and 5, between 0.9 and 5, between 1 and 5, between 2 and 5, between 3 and 5, or between 4 and 5.

In some embodiments, the tri-block polymers of the invention are of a molecular weight between 1,000 and 200,000 Da. In some embodiments, the tri-block polymers are selected to have a molecular weight of between 2,000 and 200,000, between 2,000 and 190,000, between 2,000 and 180,000, between 2,000 and 170,000, between 2,000 and 160,000, between 2,000 and 150,000, between 2,000 and 140,000, between 2,000 and 130,000, between 2,000 and 1200,000, between 2,000 and 110,000, between 2,000 and 100,000, between 2,000 and 90,000, between 2,000 and 85,000, between 2,000 and 80,000, between 2,000 and 75,000, between 2,000 and 70,000, between 2,000 and 65,000, between 2,000 and 60,000, between 2,000 and 55,000, between 2,000 and 50,000, between 2,000 and 45,000, between 2,000 and 40,000, between 2,000 and 35,000, between 2,000 and 30,000, between 2,000 and 25,000, between 2,000 and 20,000, between 2,000 and 15,000, between 2,000 and 10,000, between 2,000 and 5,000, between 2,000 and 4,000, between 2,000 and 3,000, between 7,000 and 200,000, between 4,000 and 80,000, between 1,000 and 200,000, between 1,000 and 100,000, between 1,000 and 90,000, between 1,000 and 80,000, between 1,000 and 70,000, between 1,000 and 60,000, between 1,000 and 50,000, between 1,000 and 40,000, between 1,000 and 30,000, between 1,000 and 20,000, or between 1,000 and 10,000 Da.

In some embodiments, the tri-block polymers are selected to have a molecular weight of 165,320, 86,660, 82,660, 62,280, 60,440, 47,330, 43,330, 40,760, 39,464, 32,640, 30,220, 23,732, 23,665, 22,760, 21,380, 19,732, 17,820, 15,866, 14,920, 14,856, 11,866, 11,690, 9,752, 8,928, 7,933, 5,964, 5,876 or 3,938 Da.

In some embodiments, the tri-block is a polymer of Formula (I), wherein x is between 2 and 300.

In some embodiments, the tri-blocks of the invention is a polymer having a PO/CL ratio between 0.05 and 8. In some embodiments, the ratio is between 0.1 and 5, between 0.1 and 4, between 0.1 and 3, between 0.1 and 2, between 0.1 and 1, between 0.1 and 0.9, between 0.1 and 0.8, between 0.1 and 0.7, between 0.1 and 0.6, between 0.1 and 0.5, between 0.1 and 0.4, between 0.1 and 0.3, between 0.1 and 0.2, between 0.2 and 5, between 0.3 and 5, between 0.4 and 5, between 0.5 and 5, between 0.6 and 5, between 0.7 and 5, between 0.8 and 5, between 0.9 and 5, between 1 and 5, between 2 and 5, between 3 and 5, or between 4 and 5.

In some embodiments, the tri-block of the invention is a polymer having between 10 and 2,000 caprolactone units. In some embodiments, the number of caprolactone units is between 10 and 2,000, between 10 and 1,000, between 10 and 900, between 10 and 800, between 10 and 700, between 10 and 600, between 10 and 500, between 10 and 400, between 10 and 300, between 10 and 200, between 10 and 100, between 10 and 350, between 10 and 170, between 10 and 113, between 10 and 85, between 10 and 68, between 10 and 37, between 10 and 17, between 26 and 520, between 26 and 260, between 26 and 173, between 26 and 130, between 26 and 104, between 26 and 52, between 35 and 690, between 35 and 345, between 35 and 230, between 35 and 173, between 35 and 138, between 35 and 69, between 69 and 1380, between 69 and 690, between 69 and 460, between 69 and 345, between 69 and 276, or between 69 and 138.

In some embodiments, the number of caprolactone units is selected from 1380, 690, 520, 460, 345, 340, 276, 260, 230, 173, 170, 138, 130, 113, 104, 85, 69, 68, 52, 35, 34, 26 and 17.

In some embodiments, the number of PPO units in a tri-block polymer according to the invention is 34, 52, 69 or 138.

In some embodiments, tri-block polymers according to the invention are selected amongst those listed in Table 1 below:

TABLE 1

Tri-block polymers according to the invention

| Polymer # | PPCA | PO/CL ratio | Total # of CL units | Mw 2*PCL*114 | Mw tri-block |
|---|---|---|---|---|---|
| 1 | 2000 | 0.1 | 340 | 38,760 | 40,760 |
| 2 | (34) | 0.2 | 170 | 19,380 | 21,380 |
| 3 |  | 0.3 | 113 | 12,920 | 14,920 |
| 4 |  | 0.4 | 85 | 9,690 | 11,690 |
| 5 |  | 0.5 | 68 | 7,752 | 9,752 |
| 6 |  | 1.0 | 34 | 3,876 | 5,876 |
| 7 |  | 2.0 | 17 | 1,938 | 3,938 |
| 8 | 3000 | 0.1 | 520 | 59,280 | 62,280 |
| 9 | (52) | 0.2 | 260 | 29,640 | 32,640 |

TABLE 1-continued

Tri-block polymers according to the invention

| Polymer # | PPCA | PO/CL ratio | Total # of CL units | Mw 2*PCL*114 | Mw tri-block |
|---|---|---|---|---|---|
| 10 | | 0.3 | 173 | 19,760 | 22,760 |
| 11 | | 0.4 | 130 | 14,820 | 17,820 |
| 12 | | 0.5 | 104 | 11,856 | 14,856 |
| 13 | | 1.0 | 52 | 5,928 | 8,928 |
| 14 | | 2.0 | 26 | 2,964 | 5,964 |
| 15 | 4000 | 0.1 | 690 | 78,660 | 82,660 |
| 16 | (69) | 0.2 | 345 | 39,330 | 43,330 |
| 17 | | 0.3 | 230 | 26,220 | 30,220 |
| 18 | | 0.4 | 173 | 19,665 | 23,665 |
| 19 | | 0.5 | 138 | 15,732 | 19,732 |
| 20 | | 1.0 | 69 | 7,866 | 11,866 |
| 21 | | 2.0 | 35 | 3,933 | 7,933 |
| 22 | 8000 | 0.1 | 1380 | 157,320 | 165,320 |
| 23 | (138) | 0.2 | 690 | 78,660 | 86,660 |
| 24 | | 0.3 | 460 | 52,440 | 60,440 |
| 25 | | 0.4 | 345 | 39,330 | 47,330 |
| 26 | | 0.5 | 276 | 31,464 | 39,464 |
| 27 | | 1.0 | 138 | 15,732 | 23,732 |
| 28 | | 2.0 | 69 | 7,866 | 15,866 |

Further provided are polymers according to the invention, the polymers being one or more of the polymers listed in Table 1. In some embodiments, the polymer is selected from the polymers numbered 1, 2, 3, 4, 5, 6, 7, 8, 9, 10, 11, 12, 13, 14, 15, 16, 17, 18, 19, 20, 21, 22, 23, 24, 25, 26, 27 and 28. In some embodiments, the polymer is polymer number 1, or 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28. In other embodiments, the polymer is selected from polymer number 1 and/or 2, and/or 3, and/or 4, and/or 5, and/or 6, and/or 7, and/or 8, and/or 9, and/or 10, and/or 11, and/or 12, and/or 13, and/or 14, and/or 15, and/or 16, and/or 17, and/or 18, and/or 19, and/or 20, and/or 21, and/or 22, and/or 23, and/or 24, and/or 25, and/or 26, and/or 27, and/or 28.

In some embodiments, the polymer is a polymer of Table 2, below.

The polymers according to the present invention are pre-polymerized, chain-extended and attain high molecular weight. The polymers may be optionally cross-linked. In order to increase the molecular weight of the polymer produced, the end-capped ABA tri-block or AB di-block (which may be end-capped with hydroxyl, amine, thiol or carboxylic acid groups) is chain-extended using difunctional compounds such as diisocyanate, dicarboxylic acid compounds or derivatives of dicarboxylic acids such as diacyl halides and any other group able to react with the end groups of the ABA tri-block or the AB di-block. The product which is formed from the reaction of the chain extender, coupler or cross-linking agent with the ABA tri-block or AB di-block according to the present invention will depend upon the chemical nature of the nucleophilic (or electrophilic) moieties, typically terminal, on the ABA tri-block or AB di-block (or related multi di-blocks) and the electrophilic (or nucleophilic) moieties on the chain extender, coupler or cross-linking agent. The reaction products can vary widely to produce different moieties, such as urethane groups, ester groups, urea groups and amide groups, among numerous others. For example, in the case of an ABA tri-block (hydroxyl terminated) reacting with diisocyanate chain extenders, the product is a urethane chain extended polymer. In the case of amine groups terminating the ABA tri-blocks reacted with diisocyanate chain extenders, the product is a urea. In the case of carboxylic acid groups terminating the ABA tri-blocks (which can be converted to anhydrides or acyl halides) reacting with an amine or an isocyanate terminated chain extender, coupler or crosslinking agent, the product is an amide. In some embodiments, the nucleophilic end-capped tri-blocks are chain-extended with diisocyanate compounds in order to produce chain-extended polymers according to the present invention, although the chemical approaches, as explained above, may vary greatly.

In the case of structures such as films and fibers, the chain extenders are used to provide greater molecular weight to the tri-blocks, thus enhancing mechanical properties and structural integrity.

In the case of gels, liquid polymers and/or viscous solutions, the chain extenders, couplers or cross-linking agents provide not only high molecular weight, viscosity control and structural integrity, but also a degree of water solubility/dispersibility consistent with the solubility and/or dispersibility of these polymers in water and the delivery of these polymers to a site within the patient's body. Thus, the chain extenders and couplers may be used to provide a number of benefits without using the approach of shortening the A blocks, which may hamper the beneficial morphological and mechanical effect.

The polymers according to the present invention may be cross-linked in addition to being chain-extended or coupled. Cross-linking agents may be similar to the chain extenders and couplers used in the present invention, with the exception that the cross-linking agents contain at least three reactive functional groups, in contrast with chain extenders and couplers, which contain only two reactive functional groups.

In certain aspects of the invention disclosed hereby, the A segments present ABA tri-block or the AB di-block may comprise not only a degradable component but also a component aimed at rendering the polymer with additional advantageous features. This can be exemplified by reacting the PPO B segment not only with a biodegradable component, such as a lactone, for example caprolactone, but also with, for example, a lactam, where amide groups are incorporated into the polymeric backbone. The biodegradable component and the second component, which may also be biodegradable, may be incorporated into the chain sequentially or together.

In certain aspects of the invention, the chain extender, coupler or crosslinking may comprise components aimed at rendering the polymer with additional advantageous features.

In certain aspects, chain extenders and couplers may have more than two reactive functional groups, with only two being reactive at the conditions of the chain extension or coupling reacting. The remaining unreacted reactive functional groups may remain unreacted, rendering the final polymers with additional advantageous properties, or may react under other conditions, resulting in the crosslinking of the chain extended or coupled polymer, or enabling the polymer to covalently bind to another molecule, for example a drug. This staged process may also be advantageous when manufacturing the final product consisting of polymers of the invention, capitalizing on the thermoplastic nature of the polymer, crosslinking it only at a later stage. It may also enable the binding of a bioactive molecule later in time and/or at specific regions of the product formed by polymers of the invention.

In certain aspects, the ABA tri-blocks and AB di-blocks may be end-capped with one or two double bonds, said reactive double bonds being able to react between them polymerizing and/or crossliking the polymer of the invention. The polymerization and/or crosslinking reactions may follow any of the polymerization mechanisms know and it may be triggered by any factor able to initiate the reaction. In the case of a radical polymerization reaction, the reaction may be initiated using a free radical catalysts such as benzoyl peroxide (BPO) or azobutyro nitrile (AIBN), among numerous others, or by UV radiation, in which case, the corresponding photo-initiator will be added to the system. In certain embodiments, the reaction between the C=C capped tri-blocks or di-blocks may be achieved by reacting them via other mechanisms, such as the Michael addition reaction, typically using bi-functional amines or thiols. Any of the mechanisms and pathways may be used separately or in combination with others, and while using tri-blocks and/or di-blocks, and combinations thereof.

In certain aspects of the invention disclosed hereby, the polymers may be used to manufacture fibers for use in various applications, such as in the biomedical field, in diverse areas such as medical textiles, in numerous medical devices, implants and prostheses, in wound closure arena, among numerous others. In some embodiments, polymers disclosed hereby may be used to manufacture sutures and staples.

The polymers of the invention may be fabricated into fibers having a variety of thicknesses and lengths. Fibers covering a broad range of diameters were produced, typically in the 100 micrometer (5-0 USP size) to 600 micrometer (2 USP size) range. Fibers having smaller and larger diameters may be similarly produced. The fibers produced based on polymers of the present invention had strength of several hundred MPa, typically between 300 MPa and 600 MPa.

Thus, the invention further provides a polymeric fiber, said fiber being composed of any one of the materials of the invention, or any combination thereof.

Also provided are medical devices and implants, comprising at least one polymeric material according to the invention. In some embodiments, the medical device is a suture, which retains most of its initial strength over a period that can be determined by the composition of the polymer of the invention. In some embodiments, the medical device is a suture, which retains most of its initial strength over a three- or four-month period and biodegrades over a period of six to nine months.

It is an additional object of the invention to provide biodegradable polymeric films, each film comprising a material according to the invention.

Further provided are devices in a form selected from a film, fiber, filament, mesh, membrane, rod, a coating, textile fabric, a non-woven structure or gel.

In some embodiments, the device is in a form selected from a medical textile, a medical device, an implant, a prostheses, a wound healing device, a coating, a suture, a mesh and a staple.

The invention further contemplates biodegradable polymeric objects, primarily for use in the biomedical field, having different geometries, such as, without limitation, rods, slabs, spheres and cylinders, all covering a broad range of dimensions.

Also provided are biodegradable polymeric materials of the invention for use as coatings of medical devices, where said medical devices may be polymeric, metallic, ceramic or of any other material.

It is a further object of the invention to provide a polymeric material for use as a coating of metallic medical devices, such as stents, the metallic parts of heart valves, among numerous others.

Also provided are biodegradable polymeric materials of the invention for use as covers of devices, such as metallic stents, whereby covered stents of different types are formed, using the polymers of the invention.

Also provided are biodegradable polymeric materials of the invention in fibrous configurations.

It is a further object of the invention to provide a polymeric material for use as a wound closure device, such as a suture and a staple, which may be produced in a variety of compositions, each being suitably configured or adapted for a specific utility based, inter alia, on its strength, flexibility and its biodegradability.

Thus, further contemplates are medical devices, elements or appliances comprises or consisting at least one tri-block or di-block polymer of the invention.

In some embodiments, provided is a suture made of a polymer selected from polymers of Formulae I or II or III or IV or V or the polymers of Table 1. The sutures manufactured from materials of the invention exhibit high tensile strength in vivo, supporting a wound during the healing period, while exhibiting tailored degradation. The sutures are additionally easy to handle, provide optimal knot security and are capable of holding tissue layers when knotted without being injurious to the tissue. Further, the sutures are resistant to shrinking in vivo and are absorbed with minimal or no tissue reaction after serving their purpose.

Further provided are staples for medicinal use made of a polymer selected from polymers of Formulae I or II or III or IV or V or polymers of Table 1.

The invention further provides a suture or staple according to the invention for use in a surgical procedure of a human or non-human subject.

In another aspect, the invention provides a suture for use in surgery, e.g., cosmetic surgery, aesthetic surgery, corrective surgery, soft tissue fixation, wound closure, said suture being in a form of a singular, uninterrupted, flexible, elongate filament, the filament being composed of a material according to Formulae I or II or III or IV or V or polymers of Table 1.

In some embodiments, the suture is a monofilament suture made of a single strand of a material of the invention.

In other embodiments, the suture is a multifilament suture made of a plurality of filaments, each filament being composed of a material of the invention, the materials may be the same or different. Where multifilament sutures are concerned, the individual filaments may be twisted or braided together to afford greater tensile strength, pliability and flexibility.

In some embodiments, a suture or a medical device or element of the invention may be coated with at least one coating material to increase the suture handling characteristics, degradability, stability in vivo, and other properties. The at least one coating material may be selected amongst active and non-active materials. In some embodiments, the active materials are selected from a variety of bioactive agents. Exemplary bioactive agents include, for example, anticoagulants, such as heparin and chondroitin sulphate; fibrinolytics such as tPA, plasmin, streptokinase, urokinase and elastase; steroidal and non-steroidal anti-inflammatory agents such as hydrocortisone, dexamethasone, prednisolone, methylprednisolone, promethazine, aspirin, ibuprofen, indomethacin, ketoralac, meclofenamate, tolmetin; calcium channel blockers such as diltiazem, nifedipine, verapamil; antioxidants such as ascorbic acid, carotenes and alpha-tocopherol, allopurinol, trimetazidine; antibiotics, such as noxythiolin and other antibiotics to prevent infection; pro-kinetic agents to promote bowel motility; agents to prevent collagen crosslinking such as cis-hydroxyproline and D-penicillamine; and agents which prevent mast cell degranulation such as disodium chromolglycate, among numerous others.

In addition to the above agents, which generally exhibit favorable pharmacological activity related to promoting wound healing or reducing infection or having hemostatic properties, other bioactive agents may be delivered by the polymers of the present invention include, for example, amino acids, peptides, proteins, including enzymes, carbohydrates, growth factors, antibiotics (treat a specific microbial infection), anti-cancer agents, neurotransmitters, hormones, immunological agents including antibodies, nucleic acids including antisense agents, fertility drugs, psychoactive drugs and local anesthetics, among numerous additional agents.

In some embodiments, the non-active materials are selected amongst dyes, polymeric materials, thickening agents, agents affecting hydrophilicity, agents affecting lubricity and others.

The present invention provides a great variety of suture materials, providing a surgeon with a tool-box selection of sutures that may be personalized and selected for a variety of purposes and to meet particular requirements derived from the type of surgery, the site of operation, the health of the subject operated on, and others. While most surgeons would have a preference for using a particular type of suture, unless specific circumstances dictate otherwise, a surgeon skilled in the art would know to select a suitable suture of the invention based on one or more of the following: patient-specific factors, e.g., health status, presence of infection, etc; healing characteristics of the specific tissue or organ; the period of time during which tissue support is needed and the degree of such support; as well as the type of surgical procedure, the severity of the wound and other parameters having to do with the expertise of the surgeon.

The polymers of the invention may be manufactured by any of the existing manufacturing techniques, such as extrusion, compression molding, injection molding, dip coating, solvent casting, any of the numerous 3D printing techniques, and in case the polymer will be tailored so it is compatible for the specific manufacturing technique being used.

In some embodiments of the invention, the polymeric materials are selected from ABA tri-blocks and AB di-blocks, wherein A is a biodegradable segment and B is a poly(propylene oxide) segment.

In some embodiments, the polymeric material is optionally chain extended, coupled or cross-linked using a chain extender (or bond), a coupling segment (or bond) or cross-linking segment (or bond), respectively.

In some embodiments, the polymeric material is optionally chain extended and/or coupled and/or cross-linked.

In some embodiments, A is a polymer comprising aliphatic ester units.

In some embodiments, A is a polymer comprising aliphatic ester units derived from hydroxyl acid units, their related ester or lactone.

In some embodiments, A is a polymer comprising lactic acid, lactide, glycolic acid, glycolide, or a related aliphatic hydroxycarboxylic acid or ester (lactone) selected from the group consisting of. β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxy-isovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof.

In some embodiments, A comprises poly(glycolic acid), poly(L-lactic acid), poly(D,L-lactic acid) or polycaprolactone and combinations thereof.

In some embodiments, the B block comprises hydroxyl, carboxylic acid or amine terminated polypropylene oxide segments.

In some embodiments, the ABA triblocks or AB diblocks used in the present polymers are chain extended or coupled using difunctional compounds which react with the end-cap groups of the triblocks or diblocks. In some embodiments, said difunctional compounds are diisocyanates. In some embodiments, said diisocyanates is hexamethylene diisocyanate (HDI).

In some embodiments, said difunctional chain extender or couplers comprise two molecules having the required functionality and a molecule in the middle connecting said two molecules. In some embodiments, said molecule in the middle connecting said two molecules is a polyoxyalkylene. In some embodiments, said molecule in the middle connecting said two molecules is a polyester.

In some embodiments, said polyoxyalkylene is polyethylene oxide, polypropylene oxide, polytetramethylene oxide and combinations and copolymers thereof.

In some embodiments, said polyester is polycaprolactone, polylactic acid, polyglycolic acid, and combinations and copolymers thereof.

In some embodiments, said difunctional compounds are diisocyanates. In some embodiments, said diisocyanates is hexamethylene diisocyanate (HDI).

In some embodiments, said ABA triblocks are crosslinked using a crosslinker having a functionality of three or higher.

In some embodiments, said AB diblocks are coupled using a coupler having a functionality of three or higher. In some embodiments, ABA triblocks are first chain extended and then crosslinked or coupled.

In some embodiments, the polymer of the invention is of the structure:

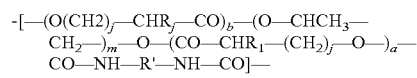

wherein a, b and m are each a positive integer, j is 0 to 10,

R' is selected from a $C_2$-$C_{12}$ alkylene group, a cycloalkyl, cycloalkyl-containing group, an aryl, an aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene, a poly(ethylene oxide) containing segment, a poly(ethylene oxide) rich chain, polypropylene, polypropylene-rich chain, a polytetramethylene, a polytetramethylene rich chain, polycaprolactone, and polycaprolactone rich chain, and $R_1$ is H or $CH_3$.

In some embodiments, R' is a hexamethylene group ($C_6$ alkylene group), j=4 and $R_1$ is H.

In some embodiments, the polymer of the invention is of the general structure:

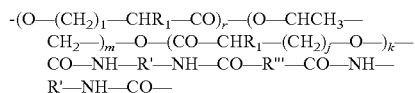
-(O—(CH$_2$)$_1$—CHR$_1$—CO)$_r$—(O—CHCH$_3$—CH$_2$—)$_m$—O—(CO—CHR$_1$—(CH$_2$)$_j$—O—)$_k$—CO—NH—R'—NH—CO—R'''—CO—NH—R'—NH—CO— wherein r, k and m are each positive integers, j is 0 to 10,

R' is selected from a C$_2$-C$_{12}$, a cycloalkyl, cycloalkyl-containing group, an aryl group, an aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene, a poly(ethylene oxide) containing segment and a poly(ethylene oxide) rich chain, R''' is a polyoxyalkylene chain comprised of a segment selected from poly(ethylene oxide), poly(ethylene oxide)-co-poly(propylene oxide), a poly(ethylene oxide) rich chain, polypropylene, a polypropylene rich chain, polytetramethylene, a polytetramethylene rich chain, polycaprolactone, and a polycaprolactone rich chain, and R$_1$ is H or CH$_3$.

In some embodiments, the chain extenders or coupling agent are of the formula:

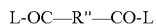
L-OC—R''—CO-L wherein

R'' is selected from a C$_0$-C$_{12}$, alkylene group, a hydroxyl or carboxylic acid substituted alkylene group, an alkene, a cycloalkyl, a hydroxyl or carboxylic acid containing cycloalkyl or cycloalkyl-containing group, an aryl or aryl-containing group or a poly(oxyalkylene) chain comprised of poly(ethylene oxide), poly(ethylene oxide)-co-poly(propylene oxide) or a poly(ethylene oxide) containing or poly (ethylene oxide) rich chains, and each L is selected from hydroxyl, a halide such as Cl, I or Br or an ester group which can be prepared from a hydroxyl group such as an alkyl, phenyl, benzyl or substituted alkyl, phenyl or benzyl group, include activated ester groups such as a tosyl group, mesyl group or related activated groups.

In some embodiments, the PO/CL ratio for polymers according to the present invention ranges from about 0.05 to about 100 or more, from about 0.1 to 100, from about 0.1 to about 30 or more, from about 0.1 to about 10, or from about 0.2 to about 10, from about 0.3 to about 10. In certain embodiments, the PO/CL ratio may fall outside of these ranges, depending upon the final characteristics of the polymers which are desired.

As used herein, the term "prepolymerized" is used to describe polymers according to the present invention which have been completely polymerized before being used, e.g., being introduced or administered to a patient to be treated. Prepolymerized polymers according to the present invention stand in contrast to polymers which may be polymerized in situ, i.e., at the site of performance in the patient. Prepolymerized polymers of the present invention are utilized to create both preformed structures, e.g., compositions having one-, two- or three-dimensional structures such as fibers, films, meshes, coating, membranes, cylinders, spheres, rods, blocks, tubes, beads, foam or rings, etc. and related structures, and non-preformed compositions such as reactive precursors, typically monomeric or oligomeric, sprays, gels, liquid polymers, viscous solutions and dispersions, among others.

The term "cross-linked" or "cross-linker" is used to describe agents, typically trifunctional or more, which covalently bond the ABA tri-blocks or AB di-blocks to other tri-blocks, di-blocks or other moieties in the present polymers. As used herein, a cross-linker refers to a chemical compound which typically contains at least three (3) reactive moieties, for example, nucleophilic and/or electrophilic moieties, or moieties such as double-bonds, which can react and crosslink the polymer. In some embodiments, cross-linking agents according to the present invention have at least three of the same type of moieties, for example nucleophilic, electrophilic or radical-initiated moieties in order to facilitate the reaction of the crosslinker with tri-blocks and di-blocks according to the present invention. In many respects, cross-linking agents are related to chain-extending agents in the present invention except that chain-extending agents contain only two reactive moieties, whereas cross-linking agents contain at least three reactive moieties.

Exemplary cross-linking agents which can be used in the present invention include those which contain at least three isocyanate moieties, for example, isocyanurates, among numerous others, or a mixture of reactive moieties, such as carboxylic acid and hydroxylic groups (an example being citric acid, among numerous others) and amine groups and combinations thereof (examples being selected amino acids and numerous oligopeptides, or numerous oligomers containing a plurality of groups able to react with the terminal groups of the triblocks and diblocks, such as an oligomer of acrylic acid. Additionally the triblocks and diblocks may be end-capped with isocyanate groups, regardless if the end group is OH, COOH, NH$_2$ or SH. This may be achieved by reacting the triblocks or diblocks with a diisocyanate, for example HDI, whereby a macrodiisocyanate able to react with said compounds, is generated. Among said compounds, any triol or above, any triacid or above, any triamine or above, and trithiol and above, and combinations thereof, generate polymers according to this invention.

Reaction of an AB di-block with a cross-linking agent may produce a star molecule or, in other instances, different structures such as a comb polymer, for example, but not a cross-linked system per se. Inasmuch as the AB di-block will generally contain only one reactive moiety per molecule (except in the case where one of the two blocks contains a blocking group which may be removed and then reacted subsequent to the initial formation of the AB di-block), the use of cross-linkers will produce predetermined structures such as star or comb molecules. The inclusion or incorporation of an additional moiety in the di-block to which a cross-linking agent can react will generate a more elaborate cross-linked system akin to that produced with the ABA tri-blocks of the present invention.

The term "non-crosslinked", "substantially non-crosslinked", "crosslinked" or "substantially crosslinked" are used to describe polymers according to the present invention which exhibit or display a substantial absence of cross-linking or, in other embodiments, substantial cross-linking. Polymers according to the present invention perform successfully in wound closure area, such as sutures and staples, as degradable reinforcing structures such as in the case of hernia meshes, as coatings of devices, prostheses and implants. In some embodiments of the invention, devices, prostheses and implants may be stents of any type, deployed in any of the systems in the body. Polymers according to the present invention which are considered substantially non-crosslinked contain less than about 1.0% cross-linking, less than about 0.5% by weight cross-linking, less than about 0.1% by weight cross-linking, less than about 0.05% by weight cross-linking are advantageously employed in the present invention. As used herein, reference to 1.0%, 0.5%, 0.1% etc cross-linking refers to the amount by weight of a cross-linker which may be found in the polymers of the present invention. In other embodiments, polymers may be cross-linked, i.e., they may contain substantially more cross-linking agent than 1.0% by weight cross-linking agent.

The polymeric compositions according to the present invention are optionally chain-extended rather than cross-linked, but may be cross-linked in addition to being chain extended. It is also possible to produce cross-linked, non-chain extended polymers according to the present invention. In certain embodiments, the polymers are both chain extended and cross-linked. In certain embodiments, the polymers are both coupled and cross-linked. In certain embodiments, the polymers are chain extended, coupled and cross-linked.

The ABA tri-blocks or AB di-blocks used in the present polymers may be chain extended. The chain extenders which are used are difunctional compounds which react with the end-cap group of the tri-blocks to produce the chain extended polymers, according to the present invention. In some embodiments chain extenders having more than two functional groups are used, provided that only two of said functional groups are able to react during the chain extension reaction. The remaining un-reacted functional groups may remain as such or will be reacted after the chain extension reaction took place on under other conditions. In some embodiments, the reactions may be conducted simultaneously, when the triblock or diblock comprises groups able to react with different groups.

In the present invention, the amount of chain extender which is included within the polymers according to the present invention may vary. Thus, the molar ratio of chain extender to ABA tri-block in the present polymers varies from about 0.5 to about 2.0 (about 1:2 to about 2:1, based upon the number of moles of difunctional chain extender and the number of moles of ABA tri-block, about 0.8 to about 1.2 or about 1.0. In the case of di-blocks, the molar ratio of chain extender to AB di-block varies from about 0.25 to about 1.0, or about 0.5 to 1.0. When used with di-blocks, the chain extenders are more accurately described as couplers, because they couple two di-blocks together to form a di-diblock. It is noted that in synthesizing the chain-extended polymers, the amount of chain extender which is reacted with difunctional tri-block or di-block to produce a polymer is generally slightly higher than the amount which is expected to be included in the final synthesized polymers. In some embodiments, couplers having more than two functional groups may be used, provided that only two of said functional groups are able to react during the coupling reaction. The remaining un-reacted functional groups may remain as such or will be reacted after the chain extension reaction took place on under other conditions. In some embodiments, the reactions may be conducted simultaneously, when the triblock or diblock comprises groups able to react with different groups.

Chain extenders which are used in the present invention, optionally contain no more than about 1% by weight of a cross-linking compound (such term signifying a compound containing at least 3 functional groups which can react with the end-cap group of the tri-block and which generally appear in a chain extender sample as a side product of the synthesis or production of the chain extender), less than about 0.5% by weight of a trifunctional compound or less than 0.1% by weight. In certain embodiments, it is possible to employ a difunctional chain extender which contains as little trifunctional (or higher functionality) compound as is practical. Also, the occurrence of side reactions which would lead to crosslinking of the polymers is negligible, due to both compositional as well as experimental parameters of the synthesis of the polymers of the present invention. Of course, in certain embodiments which separately employ cross-linking agents (either alone or in addition to chain extenders), the inclusion of weight percentages of cross-linking agents outside of the above-described weight ranges is within the scope of the present invention.

In the case of polymers which are used in structures such as fibers, coatings, meshes and films, the chain extenders may be hydrophobic. In the case of polymers which are used in systems such as hydrogels, water soluble gels, dispersions or viscous solutions, the chain-extenders may be highly water soluble. Suitable water soluble chain-extenders include, for example, polyethylene oxide diisocyanates or poly(ethylene oxide)-co-poly(propylene oxide) copolymer diisocyanates, with the polyethylene glycol or poly(ethylene oxide)-co-poly(propylene oxide) copolymer chain ranging in molecular weight from about 200 to about 20,000 or more with a preferred molecular weight ranging from about 600 to about 15,000, even more preferably about 600 to about 10,000 and even more preferably about 600 to about 3,000. In cases where the preferred embodiment is a non-water soluble polymer in a liquid form, the chain extenders may also be substantially non-water soluble. The role of the chain extenders in the hydrogels and gels and/or viscous solutions according to the present invention is to promote enhanced hydrophilicity and in some cases allow the water solubility/dispersibility of the polymers and affect their viscosity in an effort to provide polymers which are readily deliverable to a site in a patient's body and also to fine tune the kinetics of degradation, the dilution and/or the solubilization of these polymers, to obtain optimal residence time and enhance the performance of the polymer as a barrier between tissue planes.

In certain embodiments, by utilizing chain extenders rather than cross-linking agents, the present polymers are substantially non-crosslinked and have the advantage of having excellent structural integrity and characteristics such as strength and flexibility, which are advantageous for producing fibers.

The term "chain extended" is used to describe polymers according to the present invention wherein the basic tri-block or di-block is reacted with a difunctional chain extender to increase the molecular weight of the present polymers. In certain preferred embodiments, especially in the form of fibers and films, the present polymers are substantially non-crosslinked and are instead, chain-extended to provide sufficiently high molecular weight polymer chains to enhance the strength and integrity of the final polymer fiber or film compositions as well as affecting the rate of degradation.

Suitable chain extenders for use in the present invention include diisocyanates of the general formula:

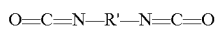

wherein

R' is selected from a $C_2$-$C_{12}$ alkylene group, a $C_2$-$C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, isophorone, lysine, 4,6'-xylylene, 3,5,5-trimethylcyclohexyl, 2,2,4-trimethylhexamethylene or p-phenylene.

Equivalents of diisocyanates may also be used as chain extenders in the present invention.

Additional chain extenders may include macrodiisocyanates including isocyanate terminated poly(oxyalkylene) including isocyanate terminated polymers comprising poly(ethylene oxide), poly(propylene oxide) and polyethylene oxide)-co-poly(propylene oxide), among others.

Additional chain extenders for use in the present invention include, for example, those according to the formula:

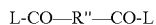

wherein

R" is selected from a $C_0$ to $C_{12}$ alkylene group, a $C_2$ to $C_8$, alkylene group, a hydroxyl or carboxylic acid substituted alkylene group, alkene, a cycloalkyl, hydroxyl or carboxylic acid-containing cycloalkyl or cycloalkyl-containing group, an aryl or aryl-containing group or a polyoxyalkylene chain comprised of poly(ethylene oxide), poly(ethylene oxide)-co-poly(propylene oxide) or other poly(ethylene oxide) rich chains, and each L is independently hydroxyl, a halide such as Cl, I or Br or an ester group which can be prepared from a hydroxyl group such as an alkyl, phenyl, benzyl or substituted alkyl, phenyl or benzyl group, including activated ester groups such as a tosyl group, mesyl group or related activating groups.

The term "strength", "mechanical strength", burst strength or "sufficient suture-holding ability" describe favorable mechanical and/or physical characteristics of the present polymers and reflect the fact that polymers for use in the present invention (generally, as fibers, or having a mechanical strength which is sufficient to form or perform in a satisfactory medical device, such as, without limitation, in the wound closure area, such as sutures, meshes and staples.

In some embodiments, the polymers according to the present invention have an Ultimate Tensile Strength value within the range of about 5-35 MPa and Elongation at Break values generally within the range of about 400-2,000%. The mechanical properties will be remarkably higher if, for example, stretched and substantially oriented to form a fiber, as disclosed below. In other embodiments the Elongation at Break displayed by polymers of the invention are much smaller, sometimes about 100%, sometimes about 50%, sometimes 20%, sometimes 5%, sometimes 2%.

The term "structure" is used to describe polymers according to the present invention which have form, size and dimensions which are established outside the body. Typically, said form, size and dimensions will not significantly change upon being placed inside the body of the patient to be treated. In other embodiments of the invention the structure does change its form, size and mechanical properties upon being placed inside the body. The term structure embraces not only flat surfaced structures (i.e., films) in the traditional manner, but also fibers, cylinders, tubes, coatings, meshes, and other three dimensional structures which are not substantially changed by the anatomy of the patient into which the structure has been placed.

In some embodiments of the present invention, the ABA tri-block or AB di-block is a unit which is generally comprised of aliphatic ester units derived from a variety of monomers as described hereinabove and comprises poly(hydroxy acid) polymers in the A block and poly(propylene oxide) polymers in the B block. The A block is however, substantially biodegradable and ranges in size from one monomeric unit up to about 400 or more monomeric units, with a size ranging from about 4 to about 50 units, about 6 to about 30 units, or about 8 to 16 units. The A block is derived from units of caprolactone, glycolic acid, lactic acid or mixtures thereof, in the form of caprolactone, glycolide or lactide reactants. The B block is poly(propylene oxide).

The ABA tri-block or AB di-block is end-capped with nucleophilic moieties such as hydroxyl or amine groups. Alternatively, these tri-blocks and di-blocks may be end-capped with carboxylate groups as well. With the nucleophilic end-capping groups in place, the ABA tri-block or AB di-block may be readily chain extended using difunctional electrophilic compounds such as diisocyanate or dicarboxylic acid compounds (or derivatives of dicarboxylic acids such as esters or diacyl halides). The tri-blocks or di-blocks are end-capped with hydroxyl groups and chain extended with diisocyanate compounds in order to produce the preferred polymers according to the present invention. In some embodiments of the invention, the triblocks and diblocks of the invention are end-capped with C=C bonds able to polymerize. In some embodiments, only one of the ends of the triblock is end-capped with a C=C, enabling the polymerization of the triblock, generating a polymer with an olefinic backbone and pendant triblock chains. The end groups of the pendant triblocks can then be left as such or used for further derivatization of the polymer, including crosslinking it or conjugating it with a suitable and advantageous bioactive molecule.

Polymers of the present invention, in a form selected from films, fibers, coatings, meshes and other preformed structures may be poly(hydroxy-carboxylic acid)/poly(propylene oxide) polymers of the chemical structure:

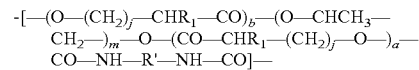

and

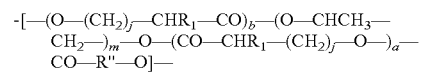

are as defined hereinabove.

The moiety

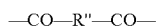

may be derived from numerous di-and tricarboxylic acids including, for example, citric acid, malic acid and tartaric acid, among numerous others such as oxalic acid, malonic acid, succinic acid, 2,3-dimethylsuccinic acid, glutaric acid, 3,3-dimethylglutaric acid, 3,3-dimethylglutaric acid, 3-methyladipic acid, adipic acid, pimelic acid, suberic acid, azelaic acid, sebacic acid, 1,9-nonanedicarboxylic acid, 1,10-decanedicarboxylic acid, 1,11-undecanedicarboxylic acid, 1,12-dodecanedicarboxylic acid, maleic acid, fumaric acid, diglycolic acid, hydromuconic acid, among others, including equivalents of these acids. These di-and tricarboxylic acids may be used to chain extend the ABA tri-blocks under controlled conditions so that cross-linking is substantially prevented. Alternatively, the use of the tricarboxylic acids may result in substantial cross-linking in certain aspects of the present invention.

In the case of using dicarboxylic acids containing additional carboxylic acid groups and/or other polar groups such as hydroxyl groups, as in the case of citric acid or malic acid, among others, these will tend to enhance the water solubility of the final polymeric compositions.

Other embodiments according to the present invention relate to polymeric compositions which have the following general structure:

—(O—(CH$_2$)$_j$—CHR$_1$—CO)$_r$—(O—CHCH$_3$—CH$_2$—)$_m$—O—(CO—CHR$_1$—(CH$_2$)$_j$—O—)$_k$—CO—NH—R'—NH—CO—R'''—CO—NH—R'—NH—CO— wherein r, k and m are positive integers, j is 0 to 10 and R''', R' is a C$_2$ to C$_{12}$, preferably a C$_2$ to C$_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain, R''' is a bifunctional chain, preferably a polyoxyalkylene chain, such as poly(ethylene oxide), poly(ethylene oxide)-co-poly(propylene oxide) or other poly(ethylene oxide) rich chains or poly(propylene oxide) chains or polycaprolactone chains, or a diol, diamine or dicarboxylic acid (an OH, NH$_2$, or COOH terminated molecule of diverse molecular weight and composition that is reactive with an isocyanate group, in certain embodiments, having at least one C=C containing molecule) or an ABA triblock wherein A is a polyester unit and B is a diol, diamine, dicarboxylic acid or a poly(oxyalkylene) containing or poly(oxyalkylene) rich chain and R$_1$ is H or CH$_3$. Examples of such compounds include, for example, OH-terminated diol molecules such as ethylene glycol, butanediol, OH-terminated polycaprolactone chains ranging in molecular weight from several hundred up to several thousand or more (4,000+), poly(propylene glycol) also ranging in molecular weight from several hundred to several thousand or more (8000+), OH-terminated polyesters or oligoesters such as OH-terminated poly(ethylene succinate) or poly(hexamethylene adipate) or polyfunctional diols such as tartaric acid (containing two OH groups which are reactive with isocyanates and two carboxylic acid groups, which, in carboxylate form, will function to enhance the overall hydrophilicity of the composition and can serve to provide a material with pH dependent water solubility).

Additional examples of such compounds include amine-containing compounds (preferably, diamine) such as ethylene diamine, hexamethylene diamine, amino acids, such as lysine (where two amine groups react leaving an unreacted carboxylic acid group and oligopeptides with two reactive amino groups, among numerous others.

Examples of difunctional carboxylic acid-containing compounds include, for example, oxalic acid, succinic acid, malic acid, adipic acid, sebacic acid, or fumaric acid, maleic acid, COOH-terminated polycaprolactone, COOH-terminated polyesters or oligoesters such as COOH-terminated poly(ethylene succinate) or poly(hexamethylene adipate). Additional examples of such compounds include, for example, C=C containing groups such as fumaric acid (trans) and maleic acid (cis) which react with the diisocyanates via their COOH groups, leaving the unreacted double bond available for further derivation by different mechanisms. More preferably, R' is a hexamethylene group (C$_6$ alkylene group), R''' is poly(ethylene oxide), j is 4 and R$_1$ is CH$_3$. The integers r and k are in some embodiments equal.

In various materials according to the present invention which are included in preformed and non-preformed materials such as fibers, films, coatings, meshes, viscous solutions, suspensions and gels, among others, the polymers may comprise ABA tri-blocks or AB di-blocks as disclosed hereinabove, which may be chain extended, coupled and/or crosslinked using a hydrophilic or highly water soluble/water dispersible chain extender or crosslinking agent. It is the hydrophilic chain extender or coupler used in various polymers according to the present invention which allows delivery of these polymer compositions in aqueous solutions.

The following chain extenders or coupling agents may be used in preparing polymers disclosed hereby:

O=C=N—R'—N=C=O wherein

R' is a C$_2$ to C$_{12}$, preferably a C$_2$ to C$_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene or p-phenylene.

Equivalents of diisocyanates may also be used as chain extenders in the present invention.

Suitable chain extenders may include water soluble macrodiisocyanates including isocyanate terminated poly(oxyalkylene) diisocyanates or isocyanate-terminated polymers comprising poly(ethylene oxide), polyethylene oxide)-co-poly(propylene oxide) and poly(ethylene oxide) containing and poly(ethylene oxide) rich chains, which may be water-soluble or non-water soluble, among others.

Additional chain extenders for use in the present invention include, example those according to the formula:

L-OC—R''—CO-L wherein R'' is a C$_0$ to C$_{12}$ alkylene group, a C$_2$ to C$_8$ alkylene group or a hydroxyl or carboxylic acid substituted alkylene group, alkene, a cycloalkyl, hydroxyl or carboxylic acid containing cycloalkyl or cycloalkyl-containing group, an aryl or aryl-containing group or a poly(oxyalkylene) chain comprised of poly(ethylene oxide), poly(ethylene oxide)-co-poly(propylene oxide) or other poly(ethylene oxide) containing or poly(ethylene oxide) rich chains and each L is hydroxyl, a halide such as Cl, I or Br or an ester group which can be prepared from a hydroxyl group such as an alkyl, phenyl, benzyl or substituted alkyl, phenyl or benzyl group, include activated ester groups such as a tosyl group, mesyl group or related activated groups. It is noted that diacids according to this aspect of the present invention may also find use as B blocks in certain ABA tri-blocks and AB di-blocks according to the present invention.

In addition to their specific objective, the present polymers may also be used to deliver bioactive compositions to a site within the patient's body. It is particularly advantageous that the present polymers may be used to deliver bioactive agents who may serve to enhance the healing of the wounds created by a surgical procedure, a disease state or other condition associated with the tissue to be treated.

Exemplary bioactive agents which may be delivered pursuant to the methods according to the present invention include, for example, anticoagulants, for example heparin and chondroitin sulphate, fibrinolytics such as tPA, plasmin, streptokinase, urokinase and elastase, steroidal and non-steroidal anti-inflammatory agents such as hydrocortisone, dexamethasone, prednisolone, methylprednisolone, promethazine, aspirin, ibuprofen, indomethacin, ketoralac, meclofenamate, tolmetin, calcium channel blockers such as diltiazem, nifedipine, verapamil, antioxidants such as ascorbic acid, carotenes and alpha-tocopherol, allopurinol, trimetazidine, antibiotics, especially noxythiolin and other antibiotics to prevent infection, prokinetic agents to promote bowel motility, agents to prevent collagen crosslinking such as cis-hydroxyproline and D-penicillamine, and agents which prevent mast cell degranulation such as disodium chromolglycate, among numerous others.

In addition to the above agents, which generally exhibit favorable pharmacological activity related to promoting wound healing or reducing infection, other bioactive agents may be delivered by the polymers of the present invention include, for example, amino acids, peptides, proteins, including enzymes, carbohydrates, antibiotics (treat a specific microbial infection), anti-cancer agents, neurotransmitters, hormones, growth factors, immunological agents including antibodies, nucleic acids including antisense agents, fertility drugs, psychoactive drugs and local anesthetics, among numerous additional agents.

The delivery of these agents will depend upon the pharmacological activity of the agent, the site of activity within the body and the physicochemical characteristics of the agent to be delivered, the therapeutic index of the agent, among other factors. One of ordinary skill in the art will be able to readily adjust the physicochemical characteristics of the present polymers and the hydrophobicity/hydrophilicity of the agent to be delivered in order to produce the intended effect. In this aspect of the invention, bioactive agents are administered in concentrations or amounts which are effective to produce an intended result. It is noted that the chemistry of polymeric composition according to the present invention can be modified to accommodate a broad range of hydrophilic and hydrophobic bioactive agents and their delivery to sites in the patient.

The invention further provides an article of manufacture, being in a structure selected from a film, a patch, a fiber, a coating, a mesh, a non-woven fabric, a staple comprising at least one material according to the invention.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-C: surgical sutures degrade too fast and offer maximum support only over a 6-8 week period (Polydioxanone) and, therefore, do not provide sufficient support during the wound healing process, in the majority of patients. FIG. 1A provides data regarding commercial sutures: comparison of loss of tensile strength by time. FIG. 1B exemplifies clinical assessment of PDS sutures versus MAXON sutures, showing in premature degradability. FIG. 1C exemplifies clinical assessment of PDS sutures versus MAXON sutures, showing unsatisfactory knotability.

DETAILED DESCRIPTION OF EMBODIMENTS

Figure 1B:
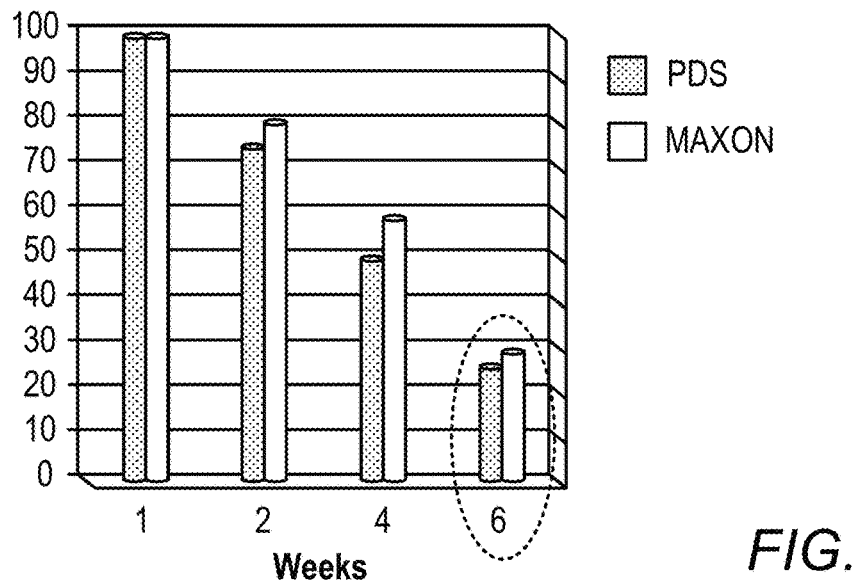

Synthesis of Polymers According to the Present Invention

In general, the synthesis of the present polymers proceeds by first synthesizing an ABA triblock or AB diblock. In this general reaction, a pre-prepared poly(propylene oxide) B block (which can be purchased or synthesized from an initiating diol and an excess of an appropriate epoxide depending upon the length of the block desired) is preferably reacted with a hydroxyacid or its cyclic lactone to produce the low molecular weight ABA triblock or AB diblock. Essentially, the poly(propylene oxide) block which is generally end-capped with hydroxyl groups or, in the case of an AB diblock is capped at one end with a hydroxyl group and at the other end with a non-reactive group, reacts with the hydroxyacid or its cyclic lactone to produce an ABA triblock or AB diblock comprising polypropylene and the biodegradable component which is end-capped with a hydroxyl group or other group(s).

Once the ABA triblock or AB diblock is formed, the hydroxyl groups at the end(s) of the molecule are reacted with difunctional chain extenders or couplers, for example, diisocyanates. This reaction produces a chain extended or coupled polymer which is readily used to prepare diverse biomedical products, such as fibers, coatings, meshes, nonwovens and films, and various related structures, gels, dispersions, suspensions, and viscous solutions of the present invention. In the case of certain polymers, these are of sufficiently low molecular weight so that they are in liquid form without the need to add a solvent.

Generally, during the first stage of the reaction in which the low molecular weight ABA triblock or AB diblock is formed, the overall molecular weight and the length of the different segments will be determined by the molecular weight of the poly(propylene oxide) block chosen to initiate the reaction, by the number of moles of hydroxyacid, its cyclic lactone or related compounds, which is reacted with the poly(propylene oxide) block and the catalyst and various experimental parameters such as the heat and the reaction time. Thereafter, the ABA triblock or AB diblock is chain extended, coupled and/or crosslinked to produce polymers containing ABA triblocks or AB diblocks.

A synthesis of the present polymers involves the use of the cyclic ester or lactone of ε-caprolactone, lactic acid and glycolic acid. The use of ε-caprolactone, lactide or glycolide as the reactant will enhance the production of ABA triblocks or AB diblocks which have relatively narrow molecular weight distributions and low polydispersity.

Once the triblock or diblock is obtained, the hydroxyl end-capped triblock or diblock is reacted with a diisocyanate, preferably hexamethylene diisocyanate and is chain extended, coupled or crosslinked.

The synthesis of the ABA triblock or AB diblock preferably proceeds by way of a ring-opening mechanism, whereby the ring opening of ε-caprolactone, lactide or glycolide is initiated by the hydroxyl end groups of the poly(propylene oxide) (PPO) chain under the influence of a tin catalyst (typically, stannous octoate). An ABA type triblock or AB type diblock is generated at this point, the molecular weight of which is a function of both the molecular weight of the central PPO chain and the length of the lateral polyester block(s). Typically, the molecular weight of the triblock spans between about 2,000 to about 60,000 (but may be as low as 1,000 or less and as high as 250,000 or more). In the case of the diblock, the molecular weight may range as low as several hundred to upwards of 50,000 or more. After synthesis of the ABA triblock or ABA diblock, the final polymer is preferably obtained by chain extending the hydroxyl terminated triblocks with difunctional reactants such as isocyanates, most preferably hexamethylene diisocyanate.

The chemical and physical properties of the different polymers will vary as a function of different parameters, the molecular weight of the PPO, the composition, morphology and molecular weight of the polyester segments present along the backbone being of particular importance, as well as the chain extender, coupler or crosslinker.

The method has several advantageous characteristics including:

A rapid, nearly quantitative reaction which is complete in from 1 to 3 hours;

The reaction takes place under moderate reaction conditions (140° C.) thus minimizing side reactions; and The resulting tri-block or di-block contains a narrow polydispersity (typically, DP=1.4-1.6 or better.

The structures to be engineered, such as fibers, coating, meshes and films, among numerous others, for use in the present invention are prepared by first producing the polymer according to the present invention and then manufacturing the product, via different manufacturing processes, among many others, by dissolving the polymer in a suitable solvent, such as chloroform, methylene chloride, dioxane, tetrahydrofuran or a related organic solvent. Films, for example, are preferably prepared by placing the solution containing polymer in a mold or a related receptacle and then allowing the solvent to evaporate. The resulting film is homogeneous and of uniform thickness and density. The film may be used as prepared or cut into segments for application to a desired site in a patient. In addition to the above-described solvent cast method, a continuous solvent cast process, as well as thermal cast method or other methods routinely used in the industry and well known in the art, such as extrusion, among many others, may be used to make the different devices, such as fibers, films and other structures according to the present invention. In order to prepare other three dimensional structures of polymer, such as cylinders and related shapes, these may be cast or molded using various techniques, starting with solid polymer. Methods to produce these structures using these techniques are well known in the art.

Currently, there are over 50 million laparotomies conducted each year world-wide. In general, closure of the muscle layer of the abdomen is performed using absorbable sutures which should provide enough mechanical support for the tissue, until natural healing occurs and scar stability is achieved. Reports in the medical literature describe the normal healing time of this fascia layer as requiring 8 weeks of support, to recover 80% of its pre-surgery burst strength.

As these tests were made in healthy subjects, literature today is showing that the fascia of immuno-suppressed patients which are the majority of patients requires significantly more time to heal. For example, a delay in fascia wound-healing of around 35% in liver transplant patients has been reported.

Figure 1C:
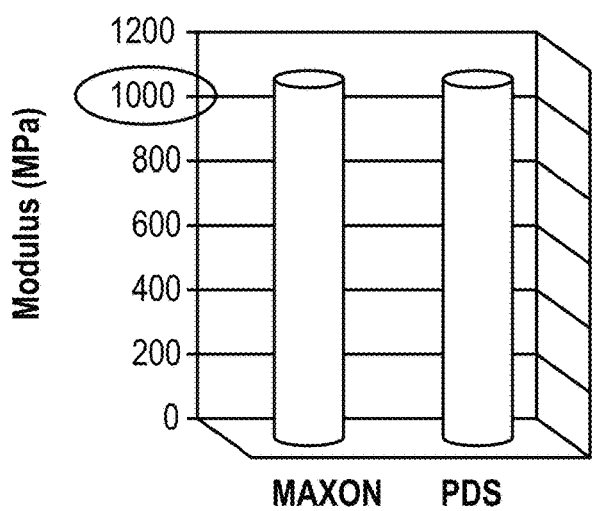

Surgical sutures today degrade too fast and offer maximum support only over a 6-8 week period (Polydioxanone) and, therefore, they do not provide sufficient support during the wound healing process, in the majority of patients (see FIGS. 1A-C).

An additional drawback of the sutures currently used in the clinic, e.g. Maxon and PDS, for this indication, is their poor knotability, most probably derived from their somewhat rigid polymeric backbone.

One aspect of the present invention was, therefore, to develop a synthetic, biodegradable suture displaying a tunable rate of degradation that provides extended support to the closure of the abdominal wall, as required following all laparatomies, minimizing the hazardous incidence of post-surgery hernias. An additional objective of this invention was to generate sutures able to generate stronger, smaller knots that better resist unravelling and that preferably generate a secure knot with less knots.

The synthesis of these block copolymers was conducted following a two-stage method, and can be exemplified for a copolymer comprising poly(propylene oxide) (PPO) and poly(caprolactone) (PCL) segments, where the poly(caprolactone) chains generate the hard blocks and poly(propylene oxide) forms the soft segments along the copolymeric chain. This copolymer is denominated PPCA. First, a PCL-PPO-PCL triblock is synthesized by the ring opening polymerization of cyclic ε-caprolactone, initiated by the hydroxyl terminal groups of the PPO chain. The second stage of the reaction involves the chain extension of the OH-terminated PCL-PPO-PCL triblock, using a bifunctional coupling agent, typically hexamethylene diisocyanate (HDI), whereby urethane groups are generated along the polymeric backbone. These polymers are called PPCA. When chain extenders having a functionality higher than two are used, the polymers obtained are crosslinked.

An important feature of the copolymers developed is their multiblock nature. The chain extension of tailor-made triblocks allowed to combine the required morphology, mainly derived from the length of both components in the tri-block, and enhanced mechanical properties, largely due to the high molecular weight copolymers obtained after the chain extension step. Each of the two components of these copolymers has, therefore, specific chemical, physical and biological roles to perform, and this modular approach affords vast versatility to these polymeric systems.

Even though a rich arsenal of sutures is available to surgeons, there are no sutures in existence that successfully address to incisions that have a mid-range healing kinetics. Basically, there are several sutures that degrade too fast for this frequently encountered clinical scenario, such as PGA, P(DL)LA, Vicryl and also PDS and Maxon, or there are long lasting sutures, degrading by far too slowly, such as those based on P(L)LA and PCL.

The paradox in this area has to do, therefore, with the large gap existing between the increasing clinical demand for mid-range biodegradable sutures, on one hand, and the lack of polymers clinically able to provide a solution to this important wound closure need, on the other hand. The lack of suitable sutures able to successfully perform in these cases has resulted, most often, in the use of sutures degrading too fast, resulting in a 10% to 20% occurrence of dangerous post-surgical incisional hernias.

The polymers disclosed hereby are can be used to manufacture new biodegradable monofilament sutures for a diversity of sites and indications, including providing a solution to this unmet clinical need. More specifically, some of the polymers of the present invention generate sutures able to retain most of their initial strength over a period of three-four months, being significantly absorbed within a period between six and nine months.

The "multicomponent" approach guiding this project allowed us to vary, quite independently, various parameters of the copolymeric system. Consequently, the properties of the different polymers can be adjusted and balanced by variations of the composition, morphology and molecular weight of their different components.

The different triblocks are characterized by GPC and NMR, to prove the occurrence of the ring opening polymerization reaction of the lactone (typically caprolactone units), initiated by PPO's OH end groups, and the composition of the resulting triblocks, respectively. This is a key step, since it is the composition of the triblock that will largely determine its morphology and rate of degradation, while the high molecular weight polymers obtained after performing the chain extension (or coupling or crosslinking) reaction, is determined by GPC. DSC and XRD analysis are used to shed light on their morphology.

Sutures of the different polymers were produced, and characterized at time zero both compositionally as well as morphologically, and their mechanical properties were measured.

The in vitro rate of degradation of the sutures was studied under pseudo-physiological conditions (saline solution, 37° C., pH 7.0). These studies included gravimetric measurements, GPC and DSC analysis, as well as measuring the mechanical properties of the polymers over time. Work was also devoted to assessing the knotability of the fibers.

Having generally described the invention, reference is now made to the following examples intended to illustrate preferred embodiments and comparisons but which are not to be construed as limiting to the scope of this invention as more broadly set forth above and in the appended claims.

Synthesis of Polymers of the Invention

1. ABA triblocks were synthesized as follows:

Polypropylene oxide (PPO, MW=2,000) was dried in vacuum overnight at 80° C. Thereafter, the PPO was cooled down to room temperature, the vacuum was broken by flushing dry $N_2$ through the system and ε-caprolactone was thereafter added in an appropriate amount (depending upon the length of the A block desired). The mixture of PPO and ε-caprolactone was placed in an oil bath at 140° C. and after 2-3 minutes (which is generally required to homogenize the system), stannous octoate was added (the catalyst/lactide mole ratio was 1/400). The mixture was then flushed with $N_2$ for a period of about 5 minutes, whereupon the $N_2$ was removed and the flask containing PPO and ε-caprolactone was capped and stirred at 140° C., in an oil bath, for 2 hours. At the end of a 2-hour period, the mixture was removed from the oil bath, was allowed to cool, dissolved in chloroform and precipitated in ether. The precipitate was thereafter collected and dried overnight in vacuum at 50° C. It was then solubilized in chloroform and the chloroform was evaporated to form a film of approximately 250 micrometer thickness.

2. The Polymer was synthesized as follows:

The synthesis of the polymers was completed by chain extending the ABA tri-blocks by reacting their hydroxyl-terminated groups with diisocyanates, typically hexamethylene diisocyanate (HDI). The tri-block obtained above was dried at 80° C. under vacuum for a period of two hours. After the two-hour period, vacuum was broken by flushing $N_2$ through the system and a minimal amount of dry dioxane was added to dissolve the tri-block. The required amount of catalyst was dissolved in dioxane (about 5 ml) and added to the tri-block. 15 ml of dry dioxane were introduced into a separation funnel and the required amount of HDI was added (the HDI:catalyst molar ratio is 5:1), and the HDI was typically in a 7-12% molar excess respective to the tri-block. The typical Tri-block:HDI:Catalyst molar ratios were, therefore, 1.0:1.07:0.2, respectively. Once the tri-block was fully dissolved, the HDI solution was added dropwise (over a period of 30 minutes) to the tri-block solution. A condenser was then connected to the reaction flask to prevent dioxane loss and the reaction was continued for a period of 2.5 hours. Then, the reaction was removed from the oil bath, allowed to cool and the polymer solution was precipitated with ether. The precipitated polymer was then collected and dried overnight at 50° C. The material was then solubilized in chloroform and the chloroform was evaporated, initially at room temperature overnight, followed by 5 hours under vacuum at 40° C., to form a film of approximately 140 μm thickness.

Table 2 below reports the Stress at Break and Modulus values of films of three polymers representative of the PPCA copolymers family

TABLE 2

Stress at Break and Modulus values of three PPCA copolymers.

| Tri-block | Stress at Break (MPa) | Modulus (MPa) |
| --- | --- | --- |
| $CL_{10}$-PPG-$CL_{10}$ | 10.7 | 18.3 |
| $CL_{15}$-PPG-$CL_{15}$ | 10.2 | 65.1 |
| $CL_{20}$-PPG-$CL_{20}$ | 16.3 | 98.0 |

Since PPO is an amorphous polymer with a very low glass transition temperature, by controlling the length of the PCL segment and, thus, its degree of crystallinity, especially flexible PPCA polymers are produced. On the other hand, by choosing shorter PPO chains, and longer, and therefore, more crystalline PCL blocks, copolymers of higher stiffness and strength are produced.

By controlling the natured and balance between the two basic components present in the copolymer and their respective length, the rate of degradation is controlled, over a wide range of time periods. The co-polymeric systems of the present invention can be rendered with a controllable degree of hydrophilicity by chain extending the PPO based tri-blocks with a hydrophilic chain extender, or coupling agent or crosslinker, in the corresponding cases. An example of this type of copolymers can be given by the OCN-HDI-$\{PEO\}_w$-HDI-NCO, where w denotes the number of ethylene oxide units present in the PEO chain.

Figure 2:
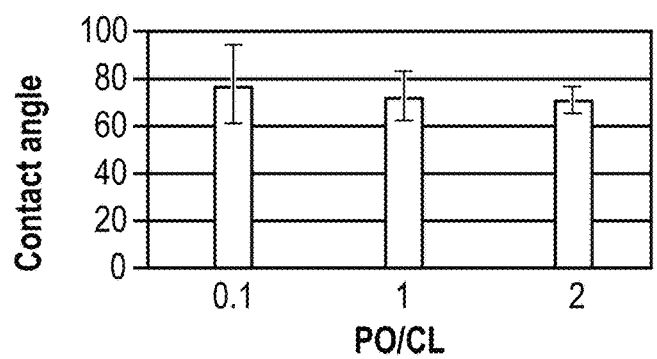
FIG. 2 presents data for a PPCA copolymer comprising PPO 2,000 segments, the length of the lateral PCL blocks decreasing, as the PO/CL ratio increases from 0.1 to 2.0. Due to the similar hydrophobicity of both components, changing the PO/CL affects only slightly the contact angle, which decreases from around 80 degrees for PO/CL=0.1, to around 70 degrees, for a PO/CL ratio of 2.0.

Fibers of the polymers of the present invention were produced by various techniques, such as extrusion and gel spinning FIG. 2 presents data for a PPCA copolymer comprising PPO 2000 segments, the length of the lateral PCL blocks decreasing, as the PO/CL ratio increases from 0.1 to 2.0. Due to the similar hydrophobicity of both components, changing the PO/CL affects only slightly the contact angle, which decreases from around 80 degrees for PO/CL=0.1, to around 70 degrees, for a PO/CL ratio of 2.0.

It is possible to fine tune the crystallinity of the polymers (data not shown).

Figure 3:
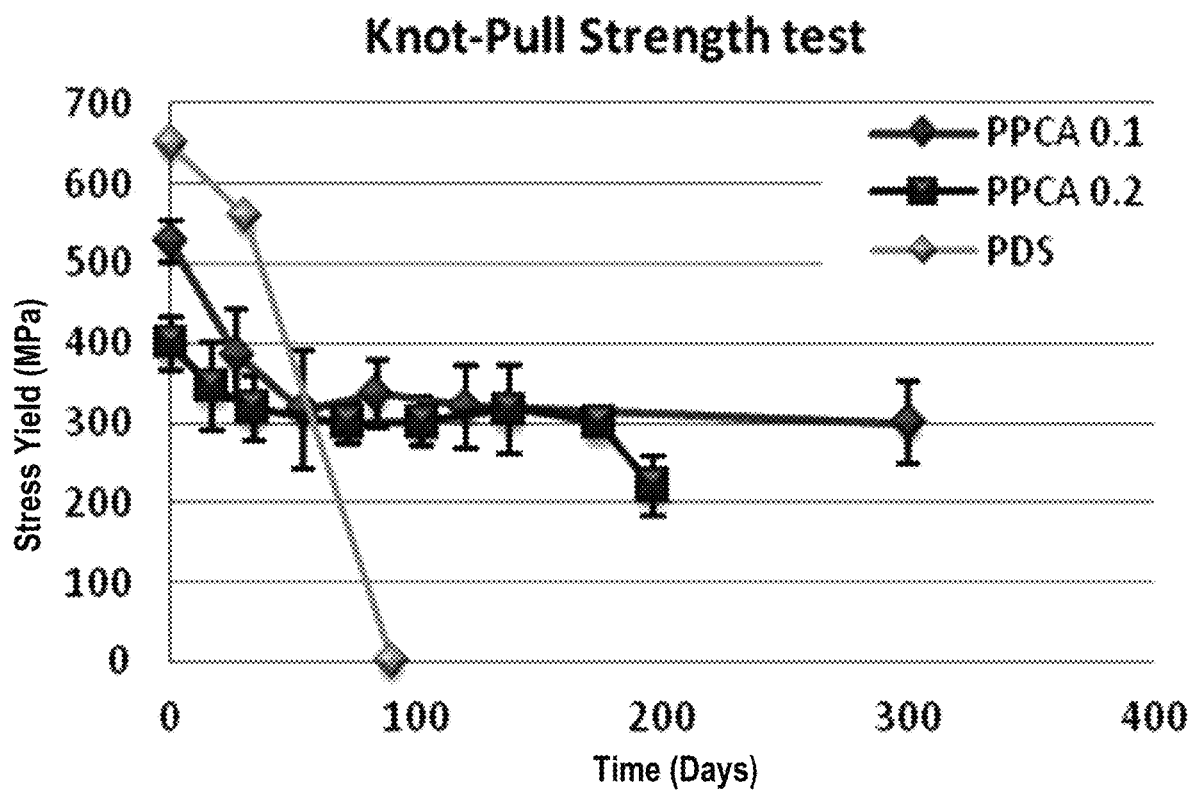
FIG. 3 presents mechanical data for both PPCA copolymers and the clinically used PDS suture, as determined by conducting the Knot-Pull test.

FIG. 3 presents mechanical data for both PPCA copolymers and the clinically used PDS suture, as determined by conducting the Knot-Pull test. It is apparent from the findings, that PPCA copolymers having low PO/CL ratios, especially 0.1 and 0.2, yield at stresses well have the 320 MPa threshold, with the PPCA 0.4 copolymer being also very close to this lower bound. It is also worth stressing that PDS shows a high Young's modulus of almost 1.5 GPa, while PPCA 0.1 and 0.2 exhibit much lower values, namely 755 MPa and 330 MPa, respectively. As will be shown below, the enhanced flexibility of PPCA backbones renders PPCA sutures with enhanced knotability.

Figure 4:
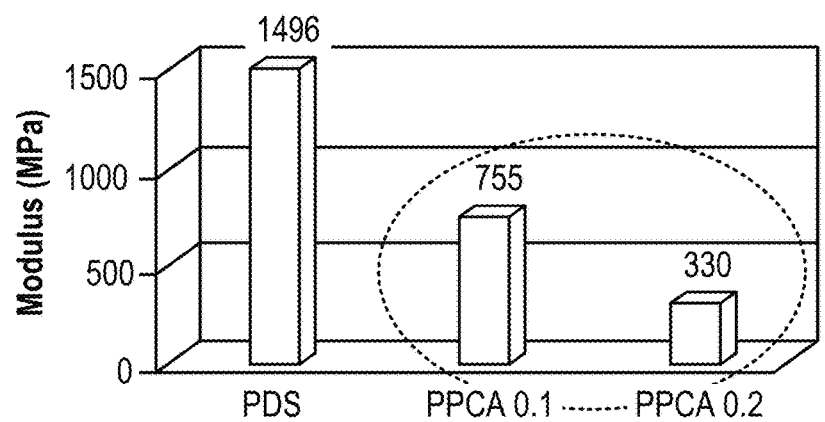
FIG. 4 shows also the decline of the mechanical properties of PDS and PPCA 0.1 and 0.2.

FIG. 4 shows also the decline of the mechanical properties of PDS and PPCA 0.1 and 0.2. While the PDS suture, currently being used clinically crosses the 320 MPa threshold already after 60 days and loses all its strength after three months, PPCA copolymers displayed a remarkably different behavior. Of special interest are PPCA 0.1 and PPCA 0.2, which remain at the 320 MPa minimal strength requirements for 300 and 180 days, respectively.

Figure 5:
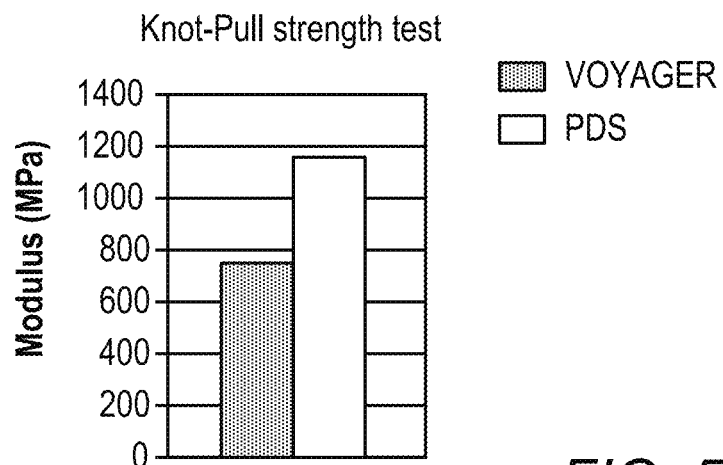
FIG. 5 presents the results of the Knot-Pull test performed on PDS and PPCA 0.1 sutures.

FIG. 5 presents the results of the Knot-Pull test performed on PDS and PPCA 0.1 sutures, highlighting the clearly superior behavior of PPCA 0.1. While PDS sutures lost all their strength prematurely (already after eight weeks), PPCA 0.1 sutures displayed a yield strength of around 350 MPa, also after 16 weeks.

Figure 6:
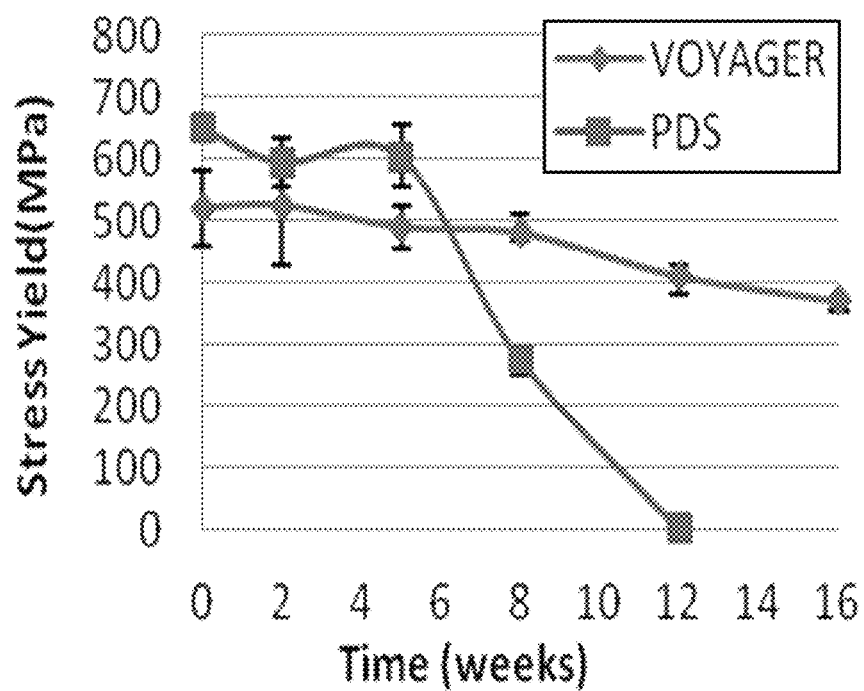
FIGS. 6 presents also a comparison between the Young's modulus of PDS, 1450 MPa, and the PPCA 0.1 suture.

FIGS. 6 presents also a comparison between the Young's modulus of PDS, 1450 MPa, and the PPCA 0.1 suture, which exhibited a modulus half as high. This difference in rigidity is responsible for the enhanced knotability of PPCA 0.1 sutures, when compared to that of PDS sutures.

While three small, tight knots are sufficient to securely knot PPCA 0.1 sutures, PDS sutures required seven knots. It is also worth stressing not only the bulkiness of knots formed by the PDS suture, but also, and even more importantly, their tendency to unravel.

The sutures were sterilized using a fully validated, low temperature (~32 degrees centigrades) ETO cycle. The sutures were manufactured following a two stage process, starting by extruding the polymer, going then through a cooling step and then stretching it substantially, to obtain the suture.

Once the sutures were manufactured, they were sent to an outside source, to connect the needles to the suture, to sterilize them and finally, to pack them. The sutures were sterilized using a fully validated, low temperature (~32 degrees centigrades) ETO cycle.

In light of the fact that incorporating PEO segments along the backbone of an aliphatic polyester was widely used to speed up the degradation of said polyester, it was totally unexpected and most surprising that copolymers of the present invention, comprising hydrophobic PPO chains, degrade at a similar rate, when compared with their PEO-containing counterparts. This is exemplified hereby by the comparison between PPCA2000/0.1 and its PEO-containing counterpart. After ~100 days in vitro degradation at 37 degrees, Knot Pull Test performed on both sutures, showed that the Stress Yield of the PPCA 2,000/0.1 suture decreased by approximately 37% (from around 520 MPa to 330 MPa), while its PEO-containing counterpart decreased by approximately 31% (from 480 MPa to around 330 MPa).

Samples of this polymer were implanted in rats near the sciatic nerve and degraded over a period of three months.

The animals study was conducted in a female rat model and PPCA 2,000/0.1 sutures were compared with the commercially available PDS suture, currently in clinical use. After the animals were anaesthetised, a longitudinal cut was performed in the abdomen and the muscle was exposed. The cut was sutured with the control (PDS) or the experimental suture (PPCA 2,000/0.1) and the skin was closed with a commercial Nylon suture. Explantations were conducted at five time points: 2, 5, 8, 12 and 16 weeks (6 rats sutured with PPC2000/0.1 and two rats sutured with PDS, at each time point), and the relevant tissues were analyzed histologically. Additionally, the sutures were inspected visually and their mechanical properties using the Knot-Pull strength and molecular weight were determined.

It was apparent from the results of the pre-clinical study that PPCA 0.1 sutures performed much better than the clinically used PDS sutures. While the PDS sutures weakened rapidly, not being able to sustain the minimal physiological 320 MPa stress, already after 8 weeks, losing all their strength after 12 weeks. In striking contrast, after 12 weeks, PPCA 0.1 sutures displayed values around 400 MPa, decreasing only slightly after four additional weeks, displaying stress yield values of around 370 MPa, after 16 weeks in vivo Also the pathological analysis of tissues surrounding the sutures after 16 weeks implantation, revealed that PPCA 0.1 performed extremely well, eliciting only a minimal inflammatory response.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

The invention claimed is:

1. A solid polymer comprising a plurality of ABA tri-blocks, wherein A is a biodegradable segment consisting of poly(caprolactone) (PCL) and B consists of a polypropylene oxide) (PPO) segment, wherein, in the polymer, the tri-blocks are linked to one another via a urethane linkage, which urethane linkage optionally includes a chain extender between urethane groups;

and wherein each tri-block has a molecular weight of between 2 KDa and 5,000 Kda.

2. A solid polymer according to claim 1 wherein said urethane linkage includes a chain extender between urethane groups.

3. A solid polymer according to claim 2 wherein said chain extender is bifunctional so as to terminate in two urethane groups.

4. A solid polymer according to claim 2, wherein said chain extender is multifunctional so as to terminate in at least three urethane groups.

5. A solid polymer according to claim 2, wherein said chain extender is hexamethylene.

6. A suture comprising a polymer according to claim 1.

7. The suture according to claim 6, being a monofilament suture or a multifilament suture.

8. The suture according to claim 7, being a monofilament suture made of a single strand of the polymer.

9. The suture according to claim 7, being a multifilament suture formed of a plurality of filaments, each filament being composed of a said polymer of the same or different composition.

10. The suture according to claim 6, coated with at least one coating material comprising active or non-active materials.

11. The suture of claim 10, wherein said coating material comprises an active material that is a bioactive agent.

12. A solid polymer according to claim 1, wherein each said ABA tri-block is a tri-block polymer selected from the group consisting of the polymers numbered 1 to 28 in Table 1:

| Polymer # | PPCA | PO/CL ratio | Total # of CL units | Mw 2*PCL*114 | Mw tri-block |
|---|---|---|---|---|---|
| 1 | 2000 | 0.1 | 340 | 38,760 | 40,760 |
| 2 | (34) | 0.2 | 170 | 19,380 | 21,380 |

| Polymer # | PPCA | PO/CL ratio | Total # of CL units | Mw 2*PCL*114 | Mw tri-block |
|---|---|---|---|---|---|
| 3 | | 0.3 | 113 | 12,920 | 14,920 |
| 4 | | 0.4 | 85 | 9,690 | 11,690 |
| 5 | | 0.5 | 68 | 7,752 | 9,752 |
| 6 | | 1.0 | 34 | 3,876 | 5,876 |
| 7 | | 2.0 | 17 | 1,938 | 3,938 |
| 8 | 3000 | 0.1 | 520 | 59,280 | 62,280 |
| 9 | (52) | 0.2 | 260 | 29,640 | 32,640 |
| 10 | | 0.3 | 173 | 19,760 | 22,760 |
| 11 | | 0.4 | 130 | 14,820 | 17,820 |
| 12 | | 0.5 | 104 | 11,856 | 14,856 |
| 13 | | 1.0 | 52 | 5,928 | 8,928 |
| 14 | | 2.0 | 26 | 2,964 | 5,964 |
| 15 | 4000 | 0.1 | 690 | 78,660 | 82,660 |
| 16 | (69) | 0.2 | 345 | 39,330 | 43,330 |
| 17 | | 0.3 | 230 | 26,220 | 30,220 |
| 18 | | 0.4 | 173 | 19,665 | 23,665 |
| 19 | | 0.5 | 138 | 15,732 | 19,732 |
| 20 | | 1.0 | 69 | 7,866 | 11,866 |
| 21 | | 2.0 | 35 | 3,933 | 7,933 |
| 22 | 8000 | 0.1 | 1380 | 157,320 | 165,320 |
| 23 | (138) | 0.2 | 690 | 78,660 | 86,660 |
| 24 | | 0.3 | 460 | 52,440 | 60,440 |
| 25 | | 0.4 | 345 | 39,330 | 47,330 |
| 26 | | 0.5 | 276 | 31,464 | 39,464 |
| 27 | | 1.0 | 138 | 15,732 | 23,732 |
| 28 | | 2.0 | 69 | 7,866 | 15,866 |

13. A medical device composed of a polymer according to claim 1.

14. The device according to claim 13, being in a form selected from the group consisting of a film, fiber, filament, mesh, membrane, rod, a coating, textile fabric, a non-woven structure, gel, a medical textile, a medical device, an implant, a prostheses, a wound healing device, a suture, a mesh and a staple.

15. A suture consisting of a polymer according to claim 1.

* * * * *